United States Patent [19]
Honjo et al.

[11] Patent Number: 5,759,810
[45] Date of Patent: Jun. 2, 1998

[54] METHOD FOR SECRETORY PRODUCTION OF PROTEIN

[75] Inventors: Masaru Honjo; Naokazu Naito; Hiroshi Uchida, all of Chiba-ken, Japan

[73] Assignee: Mitsui Toatsu Chemicals, Inc., Tokyo, Japan

[21] Appl. No.: 623,195

[22] Filed: Mar. 28, 1996

[30] Foreign Application Priority Data

Mar. 29, 1995 [JP] Japan ..................................... 7-071033

[51] Int. Cl.[6] .............................. C12P 21/06; C12P 21/04
[52] U.S. Cl. ...................... 435/69.1; 435/69.4; 435/69.7; 435/189; 530/350; 536/23.1; 536/23.2; 536/23.7
[58] Field of Search ..................... 435/69.1, 69.4, 435/69.7, 189; 530/350; 536/23.1, 23.2, 23.7

[56] References Cited

U.S. PATENT DOCUMENTS

| 4,680,262 | 7/1987 | Bochner et al. ........................... 435/68 |
| 5,496,713 | 3/1996 | Honjo et al. ........................... 435/69.4 |

FOREIGN PATENT DOCUMENTS

| 0 587 427A1 | 3/1994 | European Pat. Off. |
| WO/9409474 | 4/1994 | WIPO |
| WO94/19474 | 9/1994 | WIPO |

OTHER PUBLICATIONS

W.J. Malaisse, "The coupling of metabolic to secretory events in pancreatic islets. The possible role of glutathione reductase," *Biochimica et Biophysica Acta*, vol. 844 (1985), pp. 256–264.

Shaun Greer et al., "Glutathione Reductase from *Escherichia coli*: Cloning and Sequence Analysis of the Gene and Relationships to Other Flavoprotein Disulfide Oxidoreductases," *Biochemistry*, vol. 25 (1986), pp. 2736–2742.

"Efficient secretion of the authentic mature human growth hormone by *Bacillus subtilis*", *Journal of Biotechnology*, 8 (1988) 123–134, A. Nakayama et al.

"Specific Synthesis of DNA in Vitro via a Polymerase–Catalyzed Chain Reaction", *Methods in Enzymology*, vol. 155, Kary B. Mullis et al. (1987).

"Enhanced Tolerance to Photooxidative Stress of Transgenic *Nicotiana tabacum* with High Chloroplastic Glutathione Reductase Activity", *Plant Cell Physiol*, 34(1): 129–135 (1993); Mitsuko Aono et al.

"Human Growth Hormone: Complementary DNA Cloning and Expression in Bacteria", *Science*, vol. 205, 10 Aug. 1979, pp. 602–607, Joseph A. Martial et al.

"High efficiency transformation of *Escherichia coli* with plasmids", *Gene*, 96 (1990) 23–28, Hiroaki Inoue et al.

"Effects of Total Hydrophobicity and Length of the Hydrophobic Domain of a Signal Peptide on in Vitro Translocation Efficiency", *The Journal of Biological Chemistry*, vol. 267, No. 7, Mar. 5, 1992, pp. 4882–4888, Chinami Hikita et al.

"SecA Interacts with Secretory Proteins by Recognizing the Positive Charge at the Amino Terminus of the Signal Peptide in *Escherichia coli*", *The Journal of Biological Chemistry*, vol. 265, No. 14, May 15, 1990, Mitsuru Akita et al.

"Enzyme–Linked Immunoassay: Conjugation of the FAB' Fragment of Rabbit igG with β–D–Galactosidase from *E. coli* and its use for Immunoassay", *The Journal of Immunology*, vol. 116, No. 6, Jun. 1976, Kanefusa Kata et al.

"Molecular cloning of cDNA encoding, 20 kDa variant human growth hormone and the alternative splicing mechanism", *Biochimeda et Biophysica Actd* 949 (1988) 125–131, Dept. of Biochemistry, Mie University School of Medicine, Tsu, Mie (Japan), Naoki Masuda et al.

"The Release of Enzymes by Osmotic Hock from *Escherichia coli* in Exponential Phase", *The Journal of Biological Chemistry*, vol. 241, No. 13, Jul. 10, pp. 3055–3062, Nancy G. Nossal and Leon A. Heppel.

"Increasing the Efficiency of Protein Export in *Escherichia coli*", *Bio/Technology*, vol. 12, Feb. 1994, Julian Perez––Perez et al.

Uchida et al. "Secretion of authentic 20–kDa human growth hormone (20 K HGH in Escherichia coli and properties of the purified product" J. Biotechnol. 55, 101–112, Jun. 1997.

*Primary Examiner*—Robert A. Wax
*Assistant Examiner*—Nashaat T. Nashed
*Attorney, Agent, or Firm*—Burns, Doane, Swecker & Mathis, L.L.P.

[57] ABSTRACT

In producing a recombinant protein in the periplasm of *Escherichia coli*, the productivity of the target recombinant protein can be promoted by coexpressing glutathione reductase artificially with the target recombinant protein.

14 Claims, 11 Drawing Sheets

SEQUENCE LISTING ( 1 ) GENERAL INFORMATION:

( i i i ) NUMBER OF SEQUENCES: 19

( 2 ) INFORMATION FOR SEQ ID NO:1:

( i ) SEQUENCE CHARACTERISTICS:
        ( A ) LENGTH: 34 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:1:

```
Met  Gly  Leu  Gly  Lys  Lys  Lys  Lys  Leu  Leu  Leu  Leu  Leu  Leu  Ser  Ser
                    - 3 0                         - 2 5                         - 2 0
Ala  Val  Ala  Ala  Ser  Phe  Met  Ser  Leu  Thr  Ile  Ser  Leu  Pro  Gly  Val
                    - 1 5                         - 1 0                         - 5
Gln  Ala
```

( 2 ) INFORMATION FOR SEQ ID NO:2:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "chemically synthesized DNA sequence"

( x i ) SEQUENCE DESCRIPTION: SEQ ID NO:2:

```
CCTGAATTCA TGACTAAACA CTATG                                         25
```

( 2 ) INFORMATION FOR SEQ ID NO:3:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "chemically synthesized DNA sequence"

( x i ) SEQUENCE DESCRIPTION: SEQ ID NO:3:

```
AAACTGCAGT TAACGCATTG TCACG                                         25
```

( 2 ) INFORMATION FOR SEQ ID NO:4:

( i ) SEQUENCE CHARACTERISTICS:
        ( A ) LENGTH: 43 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "chemically synthesized DNA sequence"

( x i ) SEQUENCE DESCRIPTION: SEQ ID NO:4:

```
GGGGGATTTC ATATGGGTTT AGGTAAGAAA TTGACTAGTG CTG                     43
```

( 2 ) INFORMATION FOR SEQ ID NO:5:

( i ) SEQUENCE CHARACTERISTICS:
        ( A ) LENGTH: 43 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "chemically synthetized DNA sequence"

( x i ) SEQUENCE DESCRIPTION: SEQ ID NO:5:

```
CAGCACTAGT CAATTTCTTA CCTAAACCCA TATGAAATCC CCC                     43
```

( 2 ) INFORMATION FOR SEQ ID NO:6:

( i ) SEQUENCE CHARACTERISTICS:
        ( A ) LENGTH: 33 base pairs
        ( B ) TYPE: nucleic acid
        ( C ) STRANDEDNESS: double
        ( D ) TOPOLOGY: linear ( i i ) MOLECULE TYPE: other nucleic acid (A) DESCRIPTION: /desc = "chemically synthesized DNA
                    sequence"

(x i) SEQUENCE DESCRIPTION: SEQ ID NO:6:

TATGGGTTTA GGTAAGAAAA AGAAATTGTC TAG                                    33

(2) INFORMATION FOR SEQ ID NO:7:

(i) SEQUENCE CHARACTERISTICS:
                (A) LENGTH: 39 base pairs
                (B) TYPE: nucleic acid
                (C) STRANDEDNESS: double
                (D) TOPOLOGY: linear (i i) MOLECULE TYPE: other nucleic acid
                (A) DESCRIPTION: /desc = "chemically synthesized DNA
                    sequence"

(x i) SEQUENCE DESCRIPTION: SEQ ID NO:7:

TATGGGTTTA GGTAAGAAAA AGAAACTCCT ACTGTCTAG                              39

(2) INFORMATION FOR SEQ ID NO:8:

(i) SEQUENCE CHARACTERISTICS:
                (A) LENGTH: 48 base pairs
                (B) TYPE: nucleic acid
                (C) STRANDEDNESS: double
                (D) TOPOLOGY: linear (i i) MOLECULE TYPE: other nucleic acid
                (A) DESCRIPTION: /desc = "chemically synthesized DNA
                    sequence"

(x i) SEQUENCE DESCRIPTION: SEQ ID NO:8:

TATGGGTTTA GGTAAGAAAA AGAAATTGTT ACTTCCTA CTGTCTAG                      48

(2) INFORMATION FOR SEQ ID NO:9:

(i) SEQUENCE CHARACTERISTICS:
                (A) LENGTH: 51 base pairs
                (B) TYPE: nucleic acid
                (C) STRANDEDNESS: double
                (D) TOPOLOGY: linear (i i) MOLECULE TYPE: other nucleic acid
                (A) DESCRIPTION: /desc = "chemically synthesized DNA
                    sequence"

(x i) SEQUENCE DESCRIPTION: SEQ ID NO:9:

TATGGGTTTA GGTAAGAAAA AGAAATTGTT ACTTCTCCTA TTGCTGTCTA G                51

(2) INFORMATION FOR SEQ ID NO:10:

(i) SEQUENCE CHARACTERISTICS:
                (A) LENGTH: 50 base pairs
                (B) TYPE: nucleic acid
                (C) STRANDEDNESS: double
                (D) TOPOLOGY: linear (i i) MOLECULE TYPE: other nucleic acid
                (A) DESCRIPTION: /desc = "chemically synthesized DNA
                    sequence"

(x i) SEQUENCE DESCRIPTION: SEQ ID NO:10:

TATGGGTTTA GGTAAGAAAA AGAAATTGTT ACTTCTCCTA TTGTTACTTC                  50

(2) INFORMATION FOR SEQ ID NO:11:

(i) SEQUENCE CHARACTERISTICS:
                (A) LENGTH: 57 base pairs

5,759,810

23

24

-continued ( B ) TYPE: nucleic acid
        ( C ) STRANDEDNESS: double
        ( D ) TOPOLOGY: linear ( i i ) MOLECULE TYPE: other nucleic acid
        ( A ) DESCRIPTION: /desc = "chemically synthesized DNA
            sequence"

( x i ) SEQUENCE DESCRIPTION: SEQ ID NO:11:

GATCCCTAAC TAATTAAGCC CGCCTAATGA GCGGGCTTTT TTTTGCGGCC GCTCTAG       57

( 2 ) INFORMATION FOR SEQ ID NO:12:

( i ) SEQUENCE CHARACTERISTICS:
        ( A ) LENGTH: 38 base pairs
        ( B ) TYPE: nucleic acid
        ( C ) STRANDEDNESS: double
        ( D ) TOPOLOGY: linear ( i i ) MOLECULE TYPE: other nucleic acid
        ( A ) DESCRIPTION: /desc = "chemically synthesized DNA
            sequence"

( x i ) SEQUENCE DESCRIPTION: SEQ ID NO:12:

CTAGATTCTC ATGTTTGACA GCTTATCATC GATAAGCT       38

( 2 ) INFORMATION FOR SEQ ID NO:13:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "chemically synthesized DNA
            sequence"

( x i ) SEQUENCE DESCRIPTION: SEQ ID NO:13:

TTTCTCGGGC TGTGCAGGTC GTAAATC       27

( 2 ) INFORMATION FOR SEQ ID NO:14:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "chemically synthesized DNA
            sequence"

( x i ) SEQUENCE DESCRIPTION: SEQ ID NO:14:

AGATCCGGAG CAAAAACAGG AAGGC       25

( 2 ) INFORMATION FOR SEQ ID NO:15:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "chemically synthesized DNA
            sequence"

( x i ) SEQUENCE DESCRIPTION: SEQ ID NO:15:

TTTCCTTGGC CGGAAGAGAG TCAATTCAGG       30

(2) INFORMATION FOR SEQ ID NO:16:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "chemically synthesized DNA sequence"

(xi) SEQUENCE DESCRIPTION: SEQ ID NO:16:

```
AAACCCGAGT CACTGCCCGC TTTCCAGTCG                                    30
```

(2) INFORMATION FOR SEQ ID NO:17:

(i) SEQUENCE CHARACTERISTICS:
        (A) LENGTH: 62 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "chemically synthesized DNA sequence"

(xi) SEQUENCE DESCRIPTION: SEQ ID NO:17:

```
GTTCAGGCCT TCCCAACTAT ACCACTTTCG CGCCTATTCG ATAACGCAAT GCTACGTGCT   60
CA                                                                 62
```

(2) INFORMATION FOR SEQ ID NO:18:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:18:

```
AGGAACCGAA TTCATGACT                                                19
```

(2) INFORMATION FOR SEQ ID NO:19:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:19:

```
TCCTTGGCTT AAGTACTGA                                                19
```

METHOD FOR SECRETORY PRODUCTION OF PROTEIN

BACKGROUND OF THE INVENTION (i) Field of the Invention

The present invention relates to a method for producing a protein, and more specifically, it relates to a method for the secretory production of a protein by the use of a transformed strain of *Escherichia coli* by which the protein can be efficiently secreted and accumulated in the periplasm of the *Escherichia coli*.

(ii) Description of the Related Art

In recent years, a recombinant DNA technique has enabled the production of a useful protein by the use of microorganisms as hosts. Main examples of such a technique include an intracellular production method and a secretory production method.

It is known that the intracellular production method is a method in which the desired protein is produced and accumulated in cytoplasm with high productivity. However, the protein produced and accumulated in the cytoplasm is of a non-natural type in which methionine is added to the N-terminal of a natural type amino acid sequence, and the recombinant protein produced in large quantities usually becomes an insoluble form called an inclusion body, so that after an extracting operation, an incorrect higher structure is easily formed which is different from authentic structure. In the intracellular production method, therefore, a refolding step for converting the protein having the higher structure into its authentic structure is required, which means that the intricate step must be added to a manufacturing process.

On the other hand, in the above-mentioned secretory production method, the desired recombinant protein is expressed as a fusion protein (a precursor) in which a secretion signal peptide is added to the N-terminal. Since this secretion signal peptide is emzymatically deleted during transport across membrane, authentic protein can be secreted. As a result, the natural type protein is secreted. In the case of secretory production method, produced protein can possess authentic primary and higher structure. Thus, this method is better than the intracellular production method. In the secretory production method, however, a step of transport across membrance and a step of precursor processing are additionally necessary, so that its productivity is generally low. In particular, it is known that when a protein derived from a mammal is produced and secreted by the use of procaryotes, its productivity is much lower than when a protein derived from the procaryotes is produced and secreted, and a better secretory production method has been desired.

Nowadays, various factors which are correlated to the protein secretion of microorganisms have been reported, and several investigations for improvement of secretion productivity using such reported factors have been carried out. One of them is an investigation of the secretion signal peptide. It is known that the secretion signal peptide plays an important role at the early stage of a secretion step [J. Biol. Chem., Vol. 263, p. 8164–8169 (1990)]. For secretion of protein from host microorganisms, fusion protein synthesized in cytoplasm is essentially transported across the membrane and processed correctly to form authentic structure. U.S. Pat. No. 4,680,262 has disclosed a secretion signal peptide for an alkaline phosphatase or an enterotoxin as the preferable secretion signal peptide for secreting a human growth hormone (hereinafter often referred to a "hGH") having a molecular weight of about 22,000 (hereinafter referred to as "22K hGH"). In addition, it has simultaneously reported that the secretion of several eucaryotic proteins was tried by the use of the secretion signal peptide derived from procaryotes, but in some example, any protein was not synthesized and in other examples, even if the protein was expressed in the cytoplasms, it could not be secreted. This fact indicates that for each protein to be secreted, the selection of a suitable secretion signal peptide is required. An almighty secretion signal peptide which can be used for the secretion of every protein has not been found so far. Furthermore, with regard to the sequence of the secretion signal peptide, it has been recently elucidated that positive charges in the positive charge region of the N-terminal and the hydrophobicity of a central hydrophobic region are important [J. Biol. Chem., Vol. 267, p. 4882–4888 (1992)]. Some successful examples based on this knowledge are known. For example, Udaka et al. have reported that in a secretory production using *Bacillus brevis* as a host, addition of two basic amino acids (Arg) and three hydrophobic amino acids (Leu) into basic-and hydrophobic-regions of *Bacillus brevis* MWP (middle wall potein) secretion signal peptide caused efficient secretion of hGH. In this case, the accumulated hGH reached 200 mg/L. (Patent Application Wo 94/9474). Also with regard to this modification of the secretion signal peptide, however, any general guide principle is not present, and a preferable sequence must still be found by trial and error, case by case. In addition, the secretion signal peptide functions to translocate precursor fusion protein to the cytoplasmic membrane, but it is not directly involved in a next step where the precursor protein is transported across the cytoplasmic membrane for transfer from the cytoplasm to the periplasm or a culture medium. Therefore, the modification of the secretion signal peptide is effective to improve the transfer (localization) of the precursor protein to the membrane, but it is scarcely effective for the subsequent step where the protein to be secreted is passed through the cytoplasmic membrane from the cytoplasm to the periplasm or the culture medium, i.e., the effect of improvement of the secretion signal peptide is restricted in the case that the membrane passing step is a rate-determining step. To sum up, it is well known that the modification of the secretion signal peptide for the sake of the improvement of the secretion efficiency is important for the transfer of the precursor protein to the cytoplasmic membrane, which is led by its N-terminal portion. However, such a modification does not have any improvement effect in the case that a trouble is present in the subsequent membrane passing step.

Thus, in the case of the secretory production of the protein in which the cause for a low secretion efficiency is present in a step where the secreted protein is passed through the cytoplasmic membrane to be transferred from the cytoplasm to the periplasm or the culture medium, an improvement technique other than the modification of the secretion signal peptide is also required. Nowadays, several protein factors (SecA, SecB, SecD, SecE, SecF, SecY, SecG and the like) involved in protein secretion of *Escherichia coli* have been reported, and the function of each factor for the secretion has been examined in vitro. However, examples regarding its utilization in vivo have scarcely been reported. As only one example, it has been recently reported that the secretory production of an interleukin 6 (IL-6) could be improved by enhancing the expression of the SecY/E gene of *Escherichia coli* [Bio/Technology, Vol. 12, p. 178–180 (1994)]. Investigations using the protein factors involved in the secretion have not been put to practical use so far. In order to efficiently produce and secrete the different kinds of proteins, particularly the protein derived from a mammal, a

SUMMARY OF THE INVENTION

The present inventors tried the secretion of mammalian proteins in *Escherichia coli*. In this case, 22K hGH was relatively well secreted, but as to a human growth hormone with approximate molecular weight of 20,000 (hereinafter referred to as "20K hGH"), its secretion productivity was extremely low. Thus, in order to improve the secretory productivity of the 20K hGH, various investigations were conducted, using the above-mentioned known methods (the modification of the amino acid sequence of a secretion signal peptide, and the expression of genes for protein secretion). In any investigations, however, an effective secretory production method could not be found.

An object of the present invention is to provide an effective secretory production method which comprises secreting, into the periplasms of microorganisms, a recombinant protein, in particular one derived from a mammal, which is difficult to be produced and secreted in the microorganisms in the prior art methods.

The present inventors have intensively investigated for the purpose of finding a quite novel secretion promoting factor which deviates from the above-mentioned known conceptions, and as a result, it has been found that glutathione reductase (hereinafter abbreviated to as "GR") can be expressed simultaneously, i.e., coexpressed with a target recombinant protein in *Escherichia coli*, whereby the amount of the protein which is secreted into the periplasms can be remarkably improved. In consequence, the present invention has been completed on the basis of this new knowledge.

(1) The first aspect of the present invention is directed to a method for the secretory production of a recombinant protein which comprises secreting the recombinant protein into the periplasm of *Escherichia coli* as a host, said method comprising the step of artificially expressing glutathione reductase simultaneously with the target recombinant protein in the same host *Escherichia coli*.

(2) The second aspect of the present invention is directed to a method for the secretory production of a human growth hormone having approxinate molecular weight of 20,000 which comprises secreting the human growth hormone having approxinate molecular weight of 20,000 into the periplasm of *Escherichia coli* as a host, said method comprising the step of artificially expressing glutathione reductase simultaneously with the human growth hormone in the same host *Escherichia Coli*.

(3) The third aspect of the present invention is directed to a recombinant *Escherichia coli* in which a recombinant protein can be secreted into a periplasm, said recombinant Escherichia Coli being capable of artificially expressing glutathione reductase simultaneously with the target recombinant protein.

(4) The fourth aspect of the present invention is directed to a recombinant *Escherichia coli* in which human growth hormone having approxinate molecular weight of 20,000 can be secreted into a periplasm, said recombinant *Escherichia coli* being capable of artificially expressing glutathione reductase simultaneously with the human growth hormone having approxinate molecular weight of 20,000.

According to the method of the present invention, a recombinant protein which was difficult to be produced and secreted in microorganisms, particularly a recombinant protein derived from a mammal can be secreted into the periplasms of the microorganisms, whereby the recombinant protein can be efficiently produced.

Furthermore, according to the method of the present invention, the productivity of 20K hGH can be improved by a genetic recombination technique using *Escherichia coli* as a host.

The method of the present invention is also considered to improve the productivity of the recombinant protein even in intracellular production.

Figure 1:
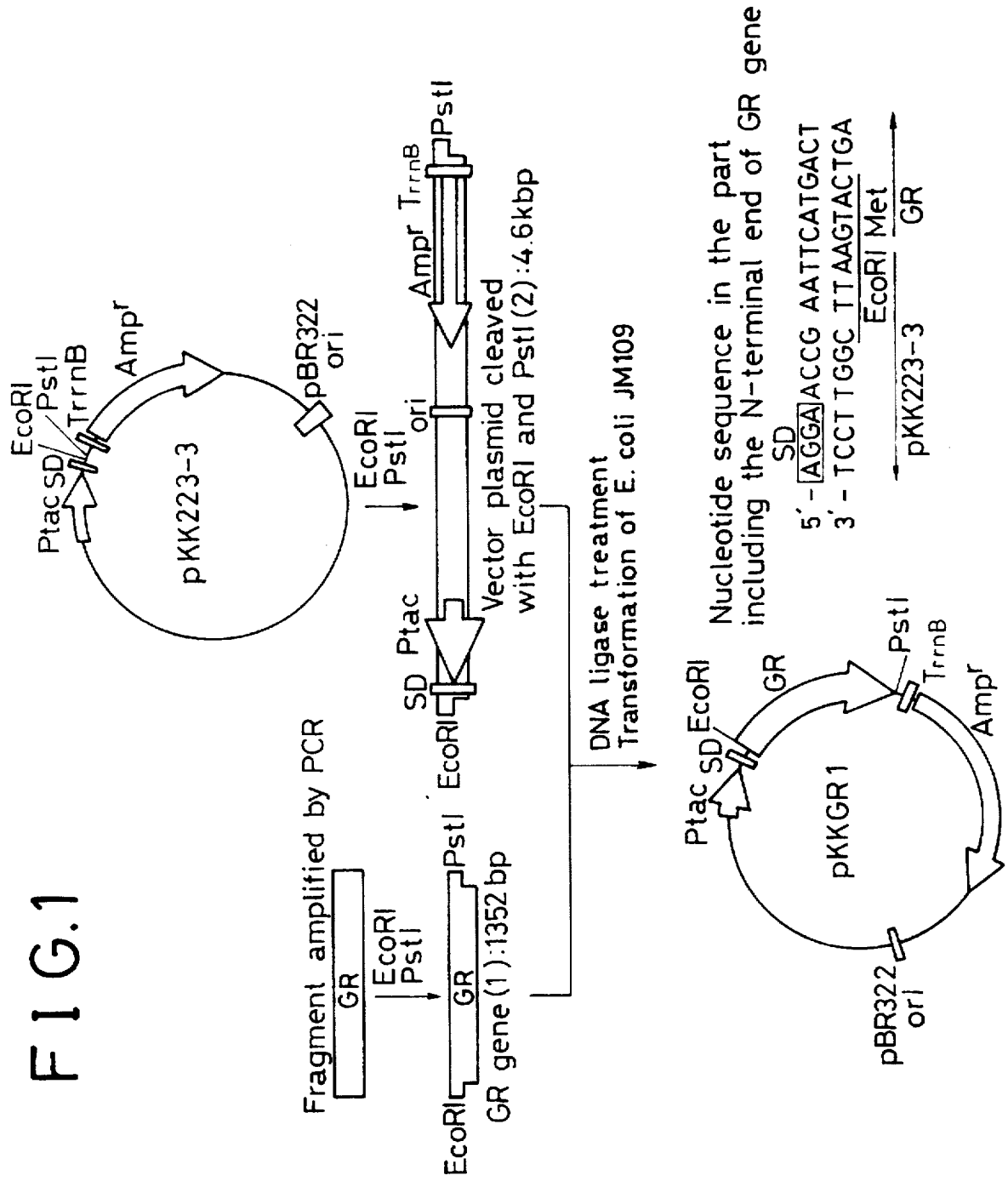
FIG. 1 is a schematic view illustrating a preparation method of a GR expressing plasmid pKKGR1.

| | |
|---|---|
| $P_{tac}$ | tac promoter region |
| SD | Ribosome binding region |
| $T_{rrnB}$ | rrnB transcription terminator region |
| Amp$^r$ | Ampicillin-resistant gene region |
| pBR322 ori | Replication origin region of pBR322 |
| GR | Glutathione reductase gene |
| $P_{NP}$ | Promoter region of a neutral protease gene of *Bacillus amyloliquefaciens* |

-continued

| | |
|---|---|
| SS | Region encoding a secretion signal peptide or a modified secretion signal peptide of the neutral protease of *Bacillus amyloliquefaciens* |
| 22K hGH | 22k hGH gene |
| pUB110 ori | Replication origin region of pUB110 |
| T$_{NP}$ | Transcription terminator region of the neutral protease gene of *Bacillus amyloliquefaciens* |
| 20K hGH | 20k hGH gene |
| Tet$^r$ | Tetracycline-resistant gene region |
| lacZ | β-galactosidase gene region |
| ColE1 ori | Replication origin region of ColE1 |
| T$_{trp}$ | Transcription terminator region of a trpA gene |
| lacI$^q$ | lacI$^q$ gene |

DETAILED DESCRIPTION OF THE INVENTION AND PREFERRED EMBODIMENTS

Now, the present invention will be described in more detail.

GR is a kind of flavin (FAD) enzyme which requires NAD(P)H as a coenzyme and which can reduce an oxidative glutathione to a reductive glutathione, and it is widely present in animal and plant tissues and microorganisms. It is known that GR produces the reductive glutathione which can reacts with disulfide bonds of a protein existing in cytoplasm, so the reductive state of its SH is maintained, or GR has a detoxicant function changing hydrogen peroxide to water. In addition, it has been reported that in a plant (Nicotianatabacum) in which GR derived from *Escherichia coli* is expressed in chloroplast, resistance to oxidation stress, which is caused by light, increases ["Plant Cell Physiol.", Vol. 34, p. 129–135 (1993)]. However, such a knowledge as in the present invention that the increased expression of the GR is involved in secretion efficiency has not been present so far.

The coexpression of a GR gene and a recombinant protein gene can be accomplished by either of a manner of allowing both the genes to exist in one replicon and a manner of allowing them to exist in different replicons, respectively. The replicon means an autonomous unit for DNA replication. "Allowing both the genes to exist in one replicon" means that both the genes exist together in a chromosome or one plasmid. "Allowing them to exist in different replicons" means that the GR gene and the recombinant protein gene exist in each of combinations of chromosome and a plasmid or two plasmids of which replicons are different.

In the present invention, the available GR gene derived from any creature can be used. Furthermore, there can also be used any known GR genes such as a cDNA obtained from an mRNA of the GR and a gene assembled by a chemical synthesis. The GR gene derived from the *Escherichia coli* are easily available and can be suitably used. In the present invention, when the GR derived from the *Escherichia coli* is used, the obtained GR gene can be allowed to coexist with the chromosome or the plasmid and the GR gene can be artificially expressed simultaneously with the recombinant protein, because the GR derived from the *Escherichia coli* is originally present in the chromosome of the *Escherichia coli*.

No particular restriction is put on the kind of recombinant protein secreted in the present invention, so far as it can be secreted in the *Escherichia coli*. Example of the recombinant protein include 22K hGH, 20K hGH and β-lactamase, and the present invention is particularly effective for the production of 20K hGH. The present inventors have already suggested a secretory production method of 20K hGH using the *Escherichia coli* in which a promoter derived from a neutral protease gene of *Bacillus amyloliquefaciens*, i.e., a secretion signal peptide gene is employed (U.S. Pat. No. 5,496,713). Accordign to the suggested method, the secretory production of 20K hGH can be improved up to about 30 mg per liter of a culture medium, but the development of a strain, by which a higher production can be obtained, has been further desired.

20K hGH has a sequence of 176 amino acids where the 32nd to 46th amino acids (15 residues) in a sequence of 191 amino acids constituting 22K hGH are lacked thereof. In recent years, although the 22K hGH has been used in clinics, much attention has been paid to the biological properties of 20K hGH as a hGH having less glucose tolerance abnormality and less leukemia origin. Hence, 20K hGH is a protein which is expected as a novel medicine hGH. Furthermore, with regard to the 14th amino acid from the N-terminal of the amino acid sequence of 20K hGH, there have been two reports, i.e., a report that it is serine and another report that it is methionine. That is to say, in Masuda, N. et al., "Biophysica Acta", Vol. 949, p. 125 (1988), a cDNA base sequence is AGT (which encodes serine), and in Martial, J. A. et al., "Science", Vol. 205, p. 602 (1979), a mRNA for the 20K hGH included a sequence for the 14th amino acid from the N-terminal is AUG (which encodes methionine). The 20K hGH of the present invention means both of the amino acid sequence that the 14th amino acid is methionine and the amino acid sequence that the 14th amino acid is serine. In addition, the amino acid sequence in which 1 or 2 amino acids are replaced, lacked, inserted or deleted is also within the category of the 20K hGH of the present invention.

No particular restriction is put on the kind of secretion signal peptide, and the secretion signal peptide derived from any secreted protein is usable. However, the preferable secretion signal peptide should be selected in consideration of the kind of protein to be secreted. For the sake of the secretory production of 20K hGH, the secretion signal peptide derived from a neutral protease of the *Bacillus amyloliquefaciens* is preferable, as described in U.S. Pat. No. 5,496,713. For the purpose of discovering an amino acid sequence which is more advantageous for the secretion of 20K hGH than the secretion signal peptide derived from the neutral protease of the *Bacillus amyloliquefaciens*, an experiment was conducted by the present inventors. That is to say, one basic amino acid, Lys, was added to the positive charge region of the N-terminal of the amino acid sequence of the secretion signal peptide and five hydrophobic amino acids, Leu, were added to the central hydrophobic region of the amino acid sequence of the secretion signal peptide to systematically assemble a 20K hGH secreting plasmids carrying various modified secretion signal peptides, as described in Comparative Example 1. Afterward, hosts of *Escherichia coli* transformed with the plasmids were cultured, and in consequence, some modified secretion signal peptides improved the amount of the secreted protein. However, if the GR gene and 20K hGH gene were simultaneously expressed in the *Escherichia coli* as shown in Example 4, the secretion improvement effect of 20K hGH having the modified secretion signal peptide was observed in all the transformed *Escherichia coli*. The sequence of the modified secretion signal peptide pGHV45 by which the highest secretion could be obtained is shown in SEQ ID NO: 1 in the sequence listing.

The GR gene is artificially expressed simultaneously with the gene for target protein to be secreted, and therefore, if the GR gene is extremely intensively expressed, the growth of the *Escherichia coli* and the secretion of the target protein are affected on occasion. Such a problem can be solved by controlling the expression of the GR gene on the basis of known information. For example, when an inducible promoter (a tac promoter, a lac promoter or the like) is used for the expression of the GR gene, there can be suitably used a manner such as the concentration decrease of an added inducer, no addition of the inducer, or the employment of a repressor gene for the promoter (e.g., lacI$^q$ for the tac promoter). The extremely excessive expression of the GR gene can be easily confirmed by carrying out the electrophoresis analysis of a solution obtained by sonicating the cultured cells.

In order to prepare the recombinant *Escherichia coli* of the present invention, (a) a DNA comprising the above-mentioned GR gene and a promoter linked therewith and/or (b) a DNA comprising a gene encoding the recombinant protein and a DNA encoding a promoter and a secretion signal sequence linked with the recombinant protein gene on the upstream side are incorporated into one replicable vector or different replicable vectors, respectively, to produce a plasmid(s), and this plasmid(s) is then introduced into the host *Escherichia coli* by means of transformation. Alternatively, the above DNAs (a) and (b) may be incorporated into a chromosome DNA together, or may be incorporated separately into a chromosome DNA and a plasmid, respectively.

As the *Escherichia coli* strain which can be used as a host in the present invention, any strain is acceptable, but the *Escherichia coli* strains which have no pathogenicity and which have often practically been used are preferable. Examples of such suitably usable strains include JM109, HB101 and W3110 (ATCC 27325). Here, the ATCC number is the number of microorganisms which American Type Culture Collection possesses, and ATCC 27325 can be sold to any one for pay on demand.

Thus, the transformed *Escherichia coli* strain can be obtained in which the protein can be efficiently secreted by the expression of the GR gene. In particular, the secretion effect of 20K hGH can be remarkably improved. An example of the strain which can secrete and produce 20K hGH is MT-10765, which is deposited under deposition No. FERM BP-5020 in National Institute of Bioscience and Human-Technology, Agency of Industrial Science and Technology at 1-1-3, Higasi, Tsukuba City, Ibaraki Prefecture, Japan. Since the MT-10765 strain can be cultured at a culture temperature of 30° C., a culture time can be shortened, and the productivity of 20K hGH is as much as 70 mg or more per liter of a culture medium.

A mechanism of the GR production in augmented amount in host cells concerning improvement of the target protein production is not clear. It is possible that the GR would be corelated to phenomenon regarding the formation of a proton gradient (a proton motive force) in a cytoplasmic membrane or an oxidation-reduction potential required in a transport step in which the protein to be secreted passes across the cytoplasmic membrane.

The transformed *Escherichia coli* strain can be cultured in a culture medium comprising a carbon source, a nitrogen source and inorganic salts which can be assimilated by the strain in accordance with a known culture technique, and as the culture technique, a liquid culture can be preferably used. The preferable culture medium is a double concentrated LB culture medium (20 g/l of polypeptone and 10 g/l of yeast extract) containing 0.2 to 1.0% glycerol.

By culturing the transformed *Escherichia coli* strain of the present invention, the secreted protein is accumulated in the periplasm of the transformed strain. The collection of the secreted protein from the periplasm of the transformed *Escherichia coli* strain can be carried out by a usual collection purification method of the protein from the periplasm, and for example, an osmotic shock procedure [Nossal G. N., "J. Biol. Chem.", Vol. 241 (13), p. 3055–3062 (1996)] or the like is usable.

Thus, according to the production method of the present invention, the desired protein can be efficiently secreted into and accumulated in the periplasm of the transformed *Escherichia Coli* strain.

Next, the present invention will be described in more detail with reference to examples, but the scope of the present invention should not be limited to these examples at all. The strains with "FERM BP-" numbers in the following Examples are deposited with the above-described "National Institute of Bioscience and Human-Technology".

EXAMPLE 1

Influence of Coexpression of GR Gene and hGH Gene on Secretion Efficiency of hGH (i) Preparation of Escherichia Coli GR gene expressing plasmid pKKGR1

A method for preparing this plasmid is shown in FIG. 1. A chromosome DNA of an *Escherichia coli* K-12 strain (ATCC 23716) was prepared. By the use of chemically synthesized oigonucleotide primers of SEQ ID NOs: 2 and 3, an GR gene was amplified in accordance with a polymerase chain reaction (PCR) method using the above-mentioned chromosome as a template [Mullis, K. B. et al; "Methods Enzymol.", Vol. 155, p. 335–350 (1987)]. As a result, a DNA segment containing a sequence ecoding the *Escherichia coli* GR gene was obtained. Next, this DNA segment was digested with restriction enzymes EcoRI and PstI to isolate a DNA fragment (1) of 1352 bp. Next, a vector plasmid pKK223-3 gotten from Pharmacia Co., Ltd. was digested with restriction enzymes EcoRI and PstI to isolate 4.6 kb of a DNA fragment (2), and this DNA fragment (2) was ligated with the above-mentioned DNA fragment (1) to prepare an *Escherichia coli* GR gene expressing plasmid pKKGR1. Afterward, an *Escherichia coli* JM109 strain (which was gotten from Takara Shuzo Co., Ltd.) was transformed in accordance with a method of Inoue H. et al. ["Gene 96", p. 23–28 (1990)] by the use of the above-mentioned plasmid to obtain a transformed *Escherichia coli* strain (MT-10771).

(2) Preparation of 22K hGH Secreting Plasmid pGHW300

Figure 2:
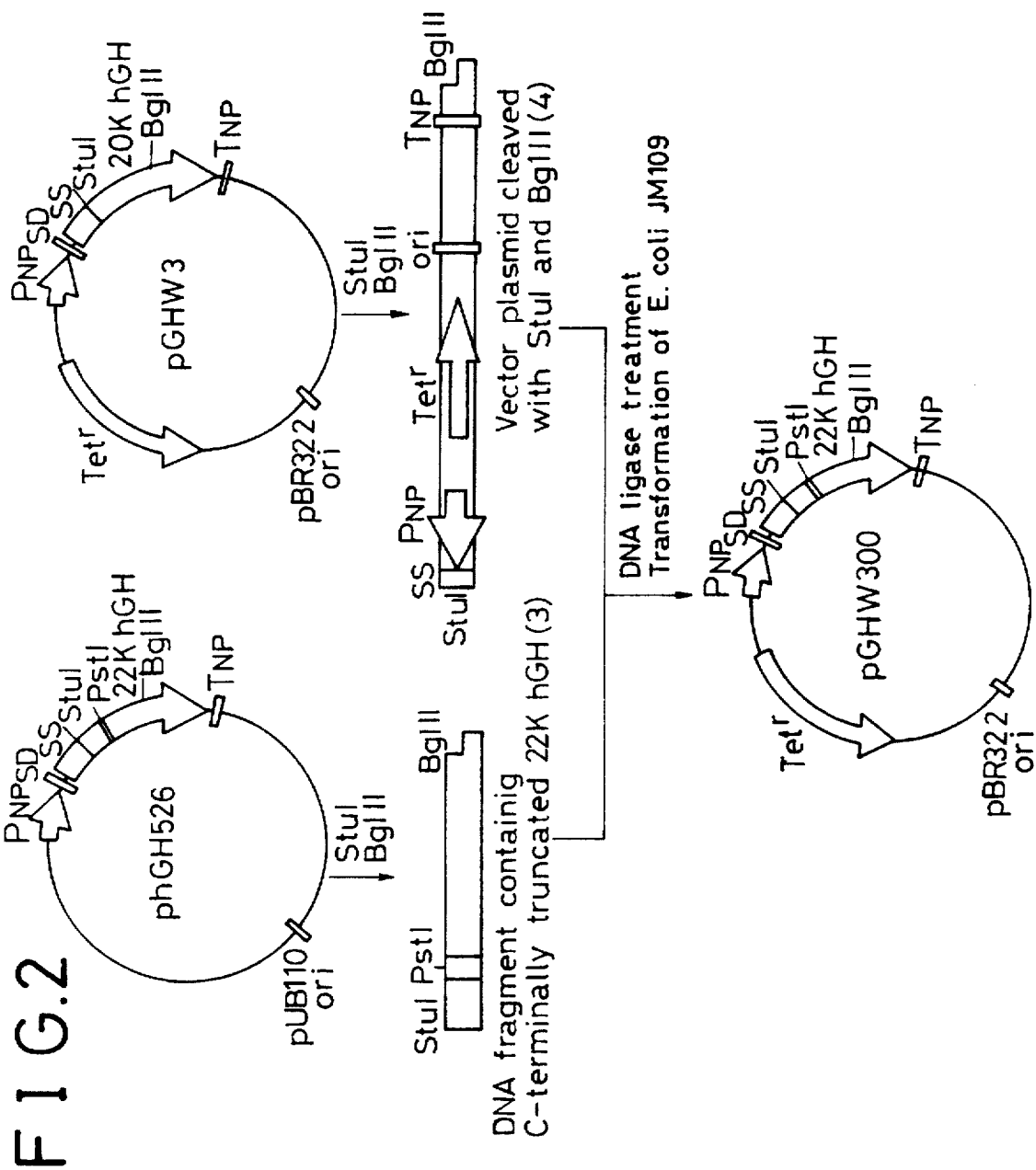
FIG. 2 is a schematic view illustrating a preparation method of a 22K hGH secreting plasmid pGHW300.

A method for preparing this plasmid is shown in FIG. 2. A 22K hGH secreting plasmid phGH526 [Nakayama A. et al.; J. Biotech, Vol. 8, p. 123–134 (1988)] used for a *Bacillus subtilis* host was digested with restriction enzymes StuI and BglII to isolate a DNA fragment (3) containing the C-terminally Truncated 22K hGH gene. On the other hand, a human 20K hGH secreting plasmid pGHW3 extracted from MT-10712 (FERM BP-4361) (U.S. Pat. No. 5,496,713) was digested with restriction enzymes StuI and BglII to obtain a vector fragment (4). This vector fragment (4) was ligated with the above-mentioned DNA fragment (3) to obtain a 22K hGH secreting plasmid pGHW300. Afterward, an *Escherichia coli* HB101 strain (which was gotten from Takara Shuzo Co., Ltd.) was transformed by the use of the above-mentioned plasmid to obtain MT-10773. The thus obtained MT-10773 is deposited under deposition No. FERM BP-5019.

(3) Coexpression of hGH Gene and GR Gene

The above plasmid pGHW3 has a DNA base sequence encoding serine as the 14th amino acid from the N-terminal of 20K hGH. On the other hand, the present inventors prepared a 20K hGH secreting plasmid pGHW30 carrying a nucleotide sequence including a codon for methionine as the 14th amino acid from the N-terminal. Concretely, a PCR amplification using a chemically synthesized oligonucleotide of SEQ ID NO: 17 and a commercially available M4 primer was carried out by the use of the plasmid pGHW3 as a template to obtain an about 0.6 kbp DNA fragment. This amplified DNA fragment was digested with restriction enzymes StuI and BglII, and then the resultant StuI-BglII fragment was replaced with the corresponding portion of the plasmid pGHW3 to prepare a 20K hGH secreting plasmid pGHW30 having a nucleotide sequence for 20K hGH having a codon encoding methionine as the 14th amino acid from the N-terminal. Furthermore, an *Escherichia coli* W3110 strain (ATCC 27325) was transformed by the use of the above-mentioned plasmid pGHW30 to obtain a transformed *Escherichia coli* strain (MT-10772). Next, the plasmid pGHW30 was extracted and purified from this transformed strain in a usual manner. Afterward, hosts of *Escherichia coli* JM109 strain were transformed with a combination of pGHW30 and pKKGR1 and a combination of pGHW300 and pKKGR1, respectively, in accordance with a method of Inoue H. et al. ["Gene 96", p. 23–28 (1990)]. Each of the transformants thus obtained was cultured at 30° C. in an LB culture medium containing 10 μg/ml of ampicillin and 10 μg/ml of tetracycline to form colonies. Next, each isolated transformant was cultured at a culture temperature of 30° C. for 24 hours in a double concentrated LB culture medium (20 g/l of polypeptone and 10 g/l of yeast extract) containing 100 μg/ml of ampicillin and 10 μg/ml of tetracycline. Since a plasmid pKK223-3 and PKKGR1 have a tac promoter, there was inspected the influence of addition of 1 mM IPTG at the start of the culture in the culture of the transformed strain having this kind of plasmid. After the culture, the hGH secreted into the periplasm fraction was collected by an osmotic shock procedure [Nossal G. N., "J. Biol. Chem.", Vol. 241 (13), p. 3055–3062 (1996)], and the concentration of the hGH in the periplasm fraction was measured by an enzyme immunoassay [Kato K. et al., "J. Immunol.", Vol. 116, p. 1554 (1976)] using an antibody to the hGH. The periplasm fraction solution was prepared as follows. That is to say, the cell pellets of the cultured *Escherichia coli* were collected in the state of a precipitation fraction by centrifuging the culture medium, and then suspended in an isotonic solution (a 10 mM trishydrochloric acid buffer solution (ph 7.0) containing 20% sucrose and 1 mM EDTA) in a 1/10 amount of the original culture medium. Afterward, the suspension was allowed to stand for 30 minutes, followed by centrifugal separation, to collect the cell pellets. Next, the thus collected cell pellets were suspended in cold water at 4° C. to extract a protein present in the periplasms of the cell pellets. The suspension was subjected to the centrifugal separation to remove the cell pellets therefrom, and the resulting supernatant liquid (an extracted component) was collected as a periplasm fraction. The concentration of the collected hGH in the periplasm fraction was measured by an enzyme immunoassay, and on the basis of a measured value, the amount of the secreted hGH per liter of the culture medium was calculated. The results are shown in Table 1 and Table 2.

TABLE 1

The improvement of the secretion amount of 20K hGH by the simultaneous expression of the GR gene (in terms of mg per liter of the culture medium)

| Plasmid | pGHW30 | pGHW30/ pKK223-3 | | pGHW30/ pKKGR1 | |
|---|---|---|---|---|---|
| Addition of IPTG | — | — | + | — | + |
| Amount of secreted 20K hGH | 30 | 24 | 19 | 30 | 65 |

TABLE 2

The improvement of the secretion amount of 22K hGH by the simultaneous expression of the GR gene (in terms of mg per liter of the culture medium)

| Plasmid | pGHW300 | pGHW300/ pKK223-3 | | pGHW300/ pKKGR1 | |
|---|---|---|---|---|---|
| Addition of IPTG | — | — | + | — | + |
| Amount of secreted 22K hGH | 60 | 37 | 29 | 61 | 105 |

When the GR gene was coexpressed with the hGH gene, both of the 20K hGH and 22K hGH could be largely secreted than when the hGH secreting plasmid alone was used. In the case that the vector plasmid pKK223-3 and the hGH secreting plasmid were allowed to exist in the same cell, the amounts of the secreted 20K hGH and 22K hGH both decreased. However, when both of the GR expressing plasmid pKKGR1 and the hGH secreting plasmid was allowed to exist in the same cell, the amounts of the secreted 20K hGH and 22K hGH both remarkably increased. This fact indicates that the coexpression of the GR gene can improve the amount of the secreted target product. The reason why, in the coexistence of the vector plasmid pKK223-3 and the hGH secreting plasmid, the amount of the secreted hGH is smaller than in the single presence of the hGH secreting plasmid is not definite, but the pKK223-3 has a replication origin derived from pBR322, as in the hGH secreting plasmid, and therefore it can be supposed that the competition of the replication and the deterioration of compatibility would occur. It can also be presumed that β-lactamase which is the drug-resistant marker of pKK223-3 is a secreted protein, and this protein would compete with a hGH precursor in a membrane passing step.

In the strain JM109 transformed with both the plasmids of the GR expressing plasmid pKKGR1 and the hGH secreting plasmid, the addition of an inducer (IPTG) for the expression of the GR was required.

EXAMPLE 2

Influence of Coexpression of GR Gene and β-Lactamase Gene on Secretion Efficiency of β-Lactamase On a vector plasmid pKK223-3 gotten from Pharmacia Labs., Inc., a β-lactamase gene is present as a drug-resistant marker. β-lactamase is expressed in cytoplasms of *Escherichia coli*, and then secreted into and accumulated in periplasm spaces. A plasmid pKKGR1 is formed by incorporating a GR gene into pKK223-3, and so it is different from pKK223-3 only in this point, and the remaining portion of the plasmid pKKGR1 is quite the same as in pKK223-3 inclusive of the expressing region of β-lactamase. Therefore, by comparing the secretion amount of β-lactamase expressed by the plasmid pKKGR1 with that of β-lactamase expressed by the plasmid pKK223-3, the influence of the simultaneous GR expression on the secretion efficiency of β-lactamase can be realized. JM109 strains transformed with the respective plasmids were cultured in the same manner as in the above-mentioned hGH producing strain, and a periplasm fraction solution was collected, subjected to SDS-PAGE, and then stained with Coomassie Brilliant Blue R250. Afterward, the band of β-lactamase (32.0 kDa) was measured by a densitometer to inspect a β-lactamase content ratio (%) with respect to the total periplasm fraction protein. The results are shown in Table 3.

TABLE 3

The influence of the coexpression of the GR gene on the secretion efficiency of β-lactamase [A660(32.0 kDa)/A660 (the total protein amount in the periplasm fraction)%]

| Plasmid | pKK223-3 | | pKKGR1 | |
|---|---|---|---|---|
| Addition of IPTG | − | + | − | + |
| β-lactamase | 10 | 8 | 18 | 24 |

It was confirmed that the secretion of β-lactamase into the periplasm of the *Escherichia coli* could also be promoted by coexpressing the GR gene.

EXAMPLE 3

Secretion and Production of 20K hGH by Use of Secretion Signal Peptide Derived from *Escherichia Coli* OmpA (1) Coexpression of GR Gene and 20K hGH Gene having Secretion Signal Peptide Coding Region Derived from *Escherichia Coli* OmpA Gene A 20K hGH secreting plasmid pGHW40 carrying a transcriptional promoter derived from the neutral protease of *Bacillus amyloliquefaciens* and a secretion signal peptide derived from an *Escherichia coli* outer membrane protein OmpA gene was transformed into an *Escherichia coli* JM109 strain together with a GR expressing plasmid pKKGR1 in the same manner as in Example 1. The thus transformed strain was cultured in the same manner as in Example 1, and a periplasm fraction was then extracted. Next, the amount of the secreted 20K hGH was measured by an enzyme immunoassay, and the results are shown in Table 4.

The same procedure was repeated except that JM109 was transformed with pGHW 40 alone.

TABLE 4

Secretion promoting effect by coexpressing GR gene, using the secretion signal peptide derived from *Escherichia coli* OmpA (in terms of mg per liter of a culture medium)

| 20K hGH vector | pGHW40 (Signal peptide of OmpA) |
|---|---|
| pKKGR1 | − | + |
| Amount of secreted 20K hGH | 2 | 16 |

For the sake of the secretion of 20K hGH, the secretion signal peptide derived from the neutral protease of the *Bacillus amyloliquefaciens* is preferable (Table 1), and the amount of the secreted 20K hGH can be remarkably increased by coexpressing the GR gene. However, even by the use of the strain transformed with the secretory plasmid having the secretion signal peptide derived from the *Escherichia coli* OmpA, the secretion efficiency could be remarkably improved owing to the coexpression of the GR gene, but the amount of the secreted 20K hGH was relatively smaller than the use of the secretion signal peptide derived from the neutral protease of *Bacillus amyloliquefaciens*. Furthermore, as shown in Example 2, the secretion promoting effect by the simultaneous expression of the GR gene can also be observed in the secretion of β-lactamase having the secretion signal peptide of β-lactamase, and in view of this fact, it is apparent that the effect of the simultaneous expression of the GR gene is not restricted by a specific kind of secretion signal peptide.

COMPARATIVE EXAMPLE 1

Production of 20K hGH by Utilization of Modified Secretion Signal Peptide Derived from Neutral Protease of *Bacillus Amyloliquefaciens*

Figure 3:
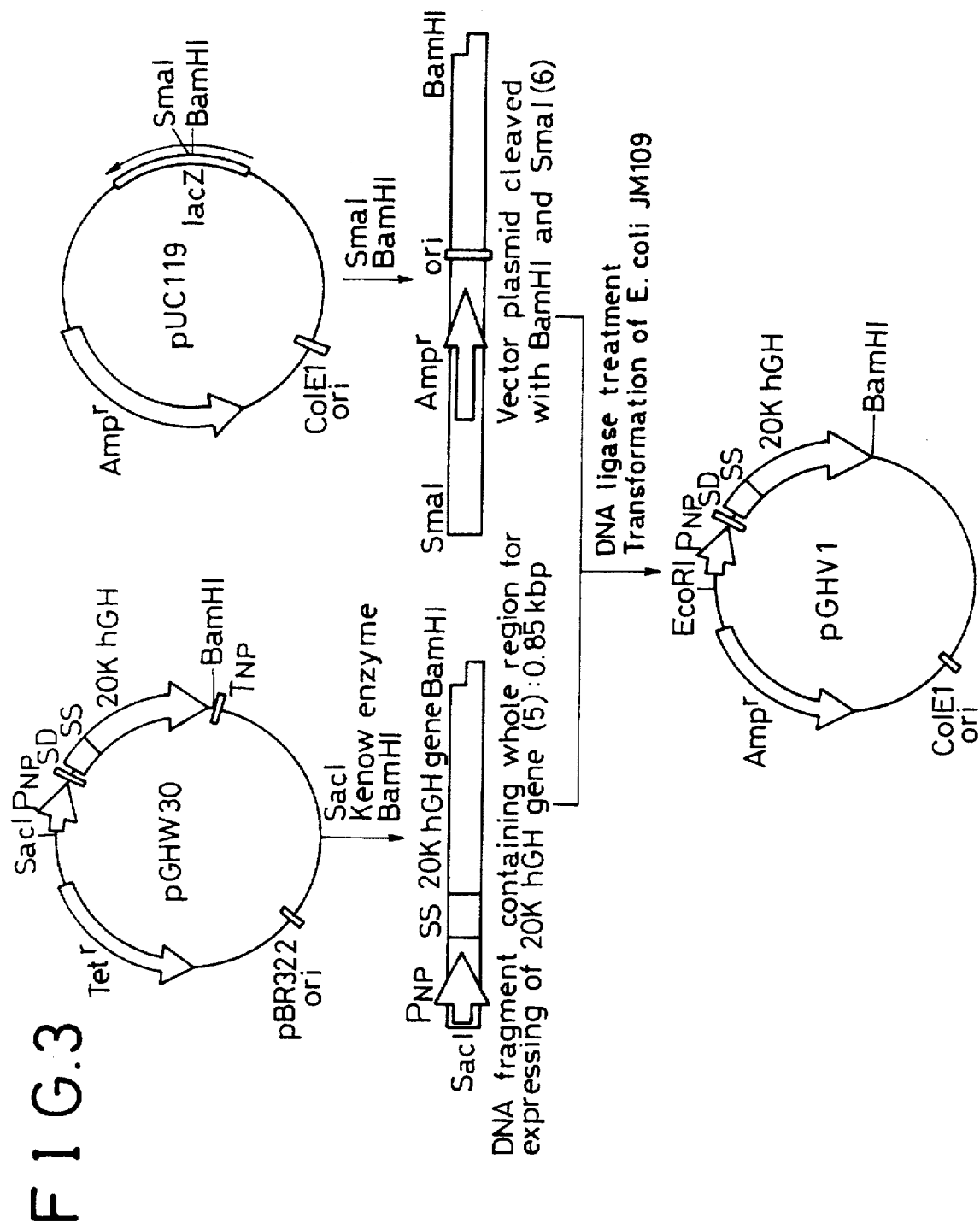
FIG. 3 is a schematic view partially illustrating a preparation method of a 20K hGH secreting plasmid pGHV1 used in the modification of a secretion signal peptide derived from the neutral protease.
Figure 4:
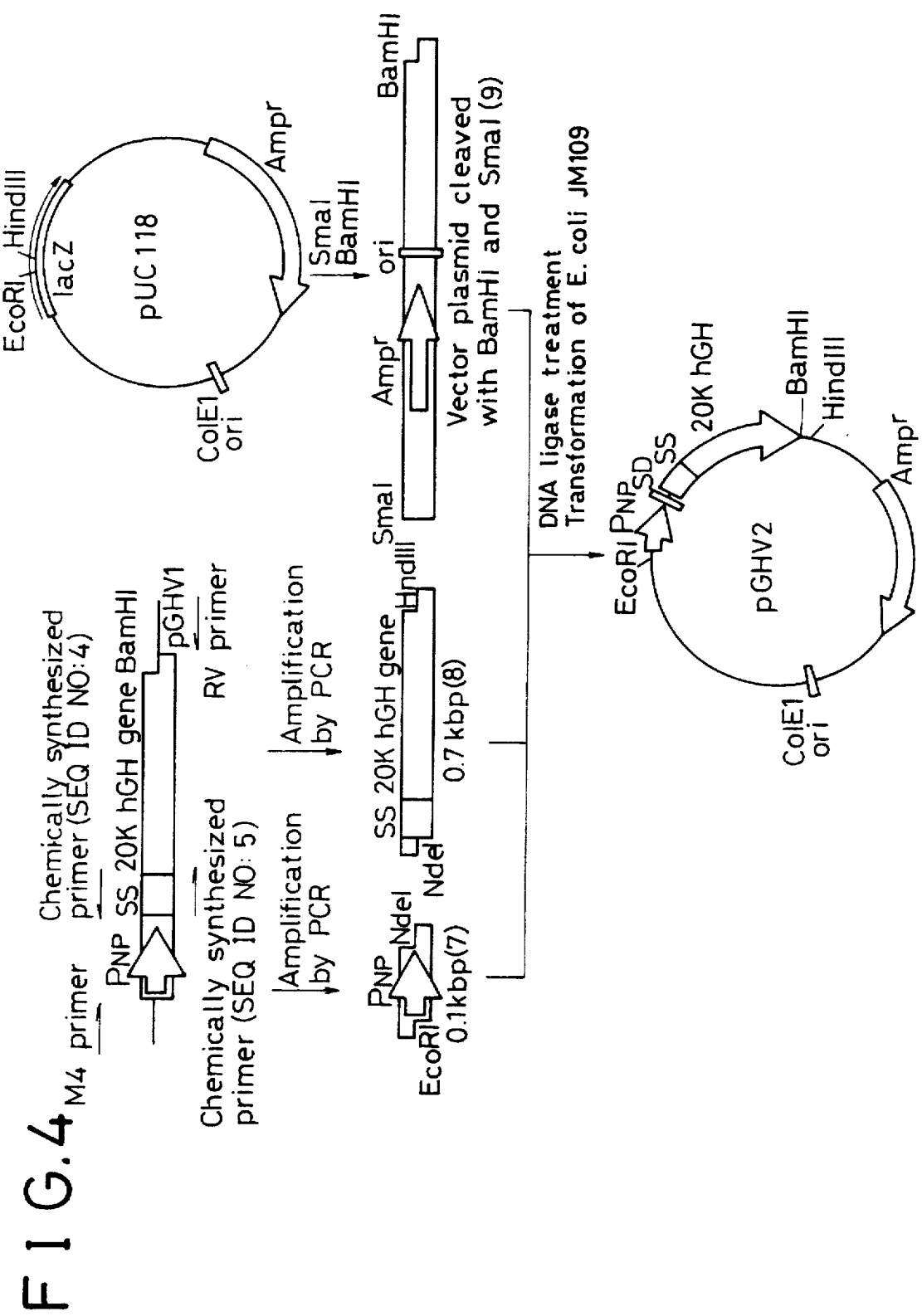
FIG. 4 is a schematic view partially illustrating a preparation method of a 20K hGH secreting plasmid pGHV2 which is used in the modification of the secretion signal peptide derived from the neutral protease.

(1) Assembly of 20K hGH Secreting Plasmid pGHV2 for Modification of Secretion Signal Peptide Derived from Neutral Protease In order to insert an optional amino acid residue into a secretion signal peptide derived from the neutral protease of *Bacillus amyloliquefaciens*, a restriction enzyme recognizing site was introduced into a secretion signal peptide sequence, and a whole plasmid was simultaneously compacted to produce a plasmid pGHV2 for the modification of the secretion signal peptide. The method is shown in FIG. 3 and FIG. 4. After pGHW 30 was digested with restriction enzyme ScaI, the terminal of the pGHW 30 was changed to a blunt end by treatment with Klenow enzyme, and a restriction enzyme BamHI was allowed to act on the pGHW 30, thereby preparing about 0.85 kbp of a DNA fragment (5) containing a promoter and a secretion signal peptide coding region, both of which are of a neutral protease gene, and a 20K hGH gene. This DNA fragment (5) was ligated with a vector portion (6), which was obtained by treatment of a commercially available cloning vector pUC119 with restriction enzymes SmaI and BamHI, in order to produce pGHV1 (FIG. 3). Next, PCR amplification using a chemically synthesized oligonucleotide of SEQ ID NO: 4 and a commercially available M4 primer was carried out by the use of this pGHV1 as a template to obtain about 100 bp of a DNA fragment (7) comprising a neutral protease gene promoter. Furthermore, the PCR amplification was carried out by using a chemically synthesized oligonucleotide of SEQ ID NO: 5 and a commercially available RV primer to obtain about 700 bp of a DNA fragment (8) containing the secretion signal peptide coding region of the neutral protease gene and the 20K hGH gene. Next, for the purpose of inserting an optional amino acid residue into the secretion signal peptide by this PCR amplification, a primer of SEQ ID NO: 5 was designed so that sites for recognizing restriction enzymes NdeI and SpeI might be contained therein. As shown in FIG. 4, the amplified DNA fragments (7) and (8) were digested with restriction enzymes EcoRI and NdeI and restriction enzymes NdeI and HindIII, respectively, and then ligated with into a vector portion (9) obtained by digesting a commercially available cloning vector pUC118 with EcoRI and HindIII, whereby pGHV2 was produced (FIG. 4). In the signal peptide derived from the neutral protease which this plasmid codes, the 8th serine (Ser) residue from the N-terminal is replaced with threonine (Thr) residue by the insertion of the restriction enzymes NdeI and SpeI recognizing sites.

Figure 5:
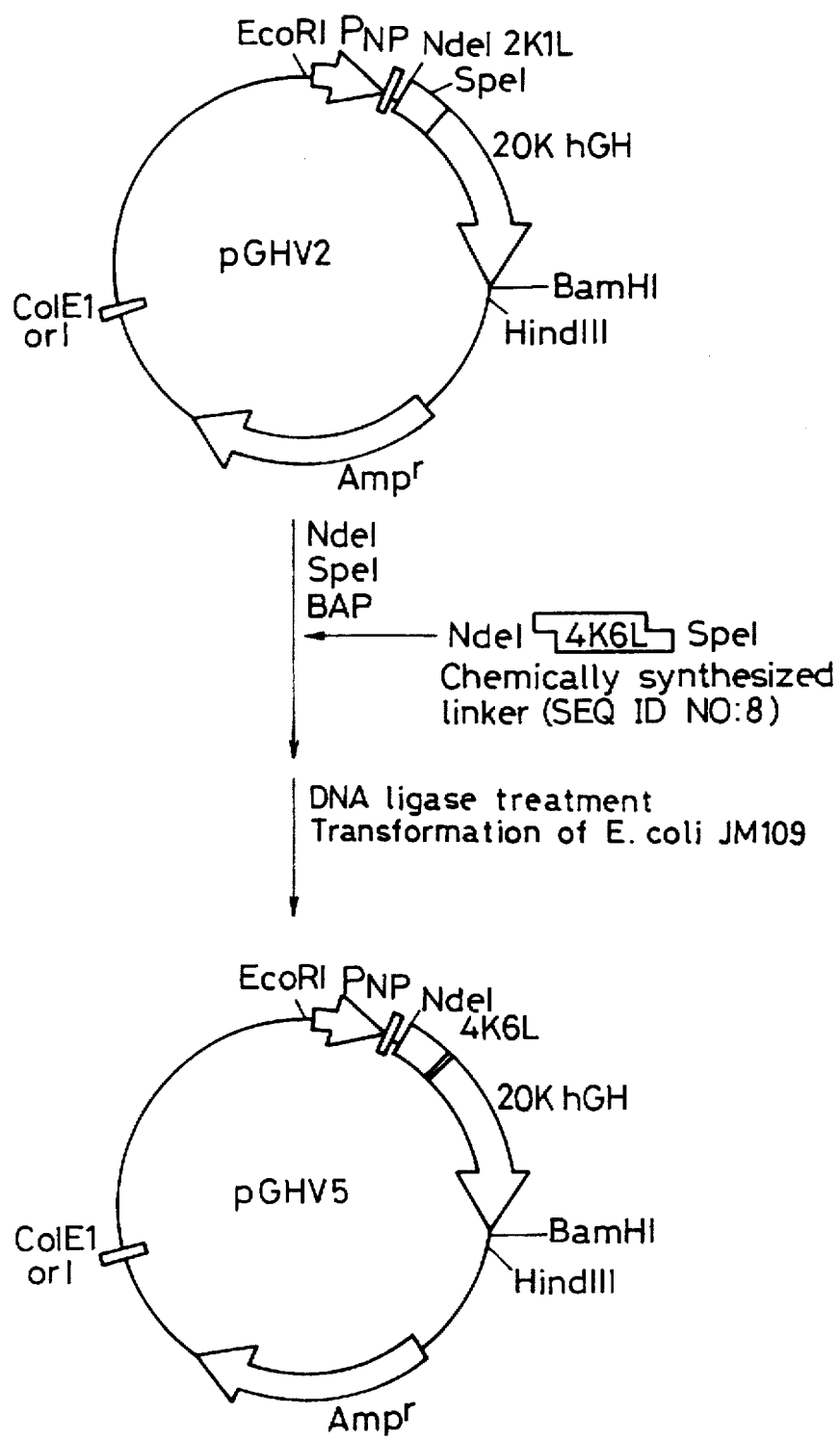
FIG. 5 is a schematic view partially illustrating a preparation method of a 20K hGH secreting plasmid having modified secretion signal peptide derived from the neutral protease.

(2) Production of 20K hGH Secreting Plasmid having Modified Secretion Signal Peptide Sequence In order to increase a positive charge region and a hydrophobic region in a secretion signal peptide sequence, positive charge amino acid(s), Lys, and hydrophobic amino acid(s), Leu, were inserted, respectively. It has been reported by Mizusima et al. that for the sake of a secretion efficiency, there is a suitable number of the hydrophobic amino acid residues constituting the hydrophobic region (Hikita C. and Mizushima S., "J. Biol. Chem.", Vol. 267, p. 4882–4888 (1992)], and therefore linker DNAs shown in SEQ ID NOs: 6 to 10 were synthesized in which the number of the leucine residues to be inserted was changed. Each synthesized linker was replaced with a region sandwiched between the restriction enzymes NdeI and SpeI of pGHV2 to produce 20K hGH secreting plasmids having different leucine residues in the secretion signal peptide sequences (pGHV3, pGHV4, pGHV5, pGHV6 and pGHV7) (FIG. 5 shows the procedure using SEQ ID NO: 8 as a representative example). The amino acid sequence in the modified secretion signal peptide sequence was confirmed by interpreting the DNA sequence encoding the amino acid residue in the secretion signal peptide sequence by the use of a fluorescent probe DNA sequence kit made by ABI Co., Ltd. After introduction of additioanl leucine residure, the threonine (Thr) residue was substituted again by the serine (Ser) reside of the above-mentioned pGHV2, and the original sequence except the inserted residue was maintained.

(3) Production of 20K hGH by Use of 20K hGH Secreting Plasmid having Modified Secretion Signal Peptide An *Escherichia coli* JM109 strain transformed with each 20K hGH plasmid having the modified secretion signal peptide obtained above was cultured in the same manner as in Example 1, and a periplasm fraction was then extracted. Afterward, the content of 20K hGH was measured, and the production of 20K hGH per liter of a culture medium was then calculated. The results are shown in Table 5. In this table, a symbol K represents the Lys residue, and a symbol L represents the Leu residue. The numbers in front of the respective symbols represent the numbers of the lysine residue and the leucine residue present in the positive charge region and the hydrophobic region after the insertion, respectively.

peptide was incorporated into the same host bacterium, and in order to measure the influence of the simultaneous expression of the GR gene on the secretion of 20K hGH, it was necessary that a drug-resistant marker having the 20K hGH secreting plasmid with the modified signal peptide should be changed from ampicillin to tetracycline. For the plasmids carrying the modified secretion signal peptide conding regions (pHGW30, pGHV2, pGHV3, pGFV4, pGHV5, pGHV6 and pGHV7), all the same operation is carried out, and therefore only the treatment of pGHV5 will be described below as a representative example.

In brief, the EcoRI-Hind III portion of pBR322 was replaced with the EcoRI-Hind III portion of pGHV5, which contained a promoter of a neutral protease gene and a region encoding a precuser composed of a modified signal peptide and 20K kGH. The cloning vector pBR322 is commercially available.

In this case, however, for the prevention of lead-through from a neutral protease promoter, a trpA terminator sequence was added immediately on the downstream side of the DNA sequence encoding the 20K hGH.

Figure 6:
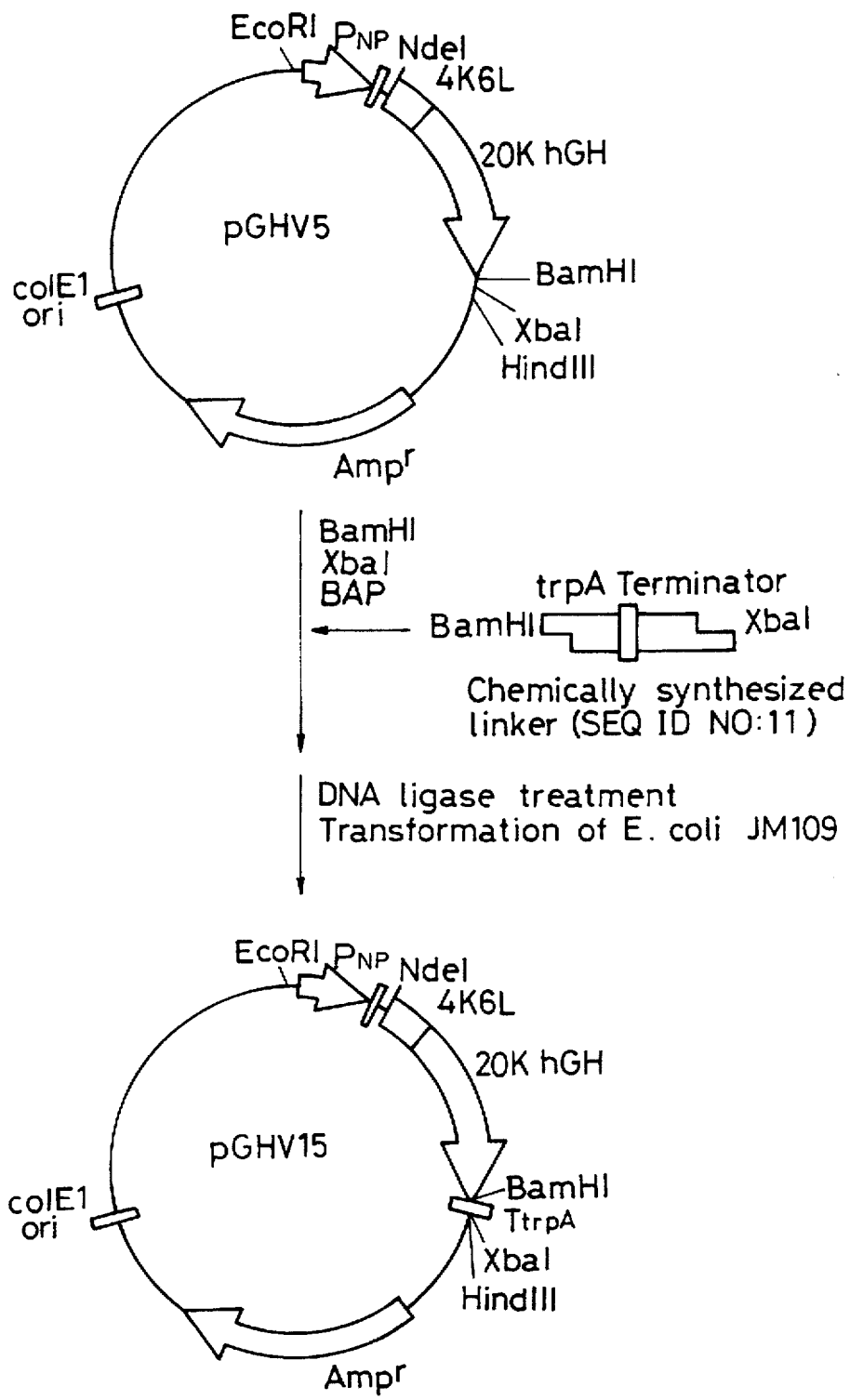
FIG. 6 is a schematic view partially illustrating a preparation method of a 20K hGH secreting plasmid having a drug-resistant marker.
Figure 7:
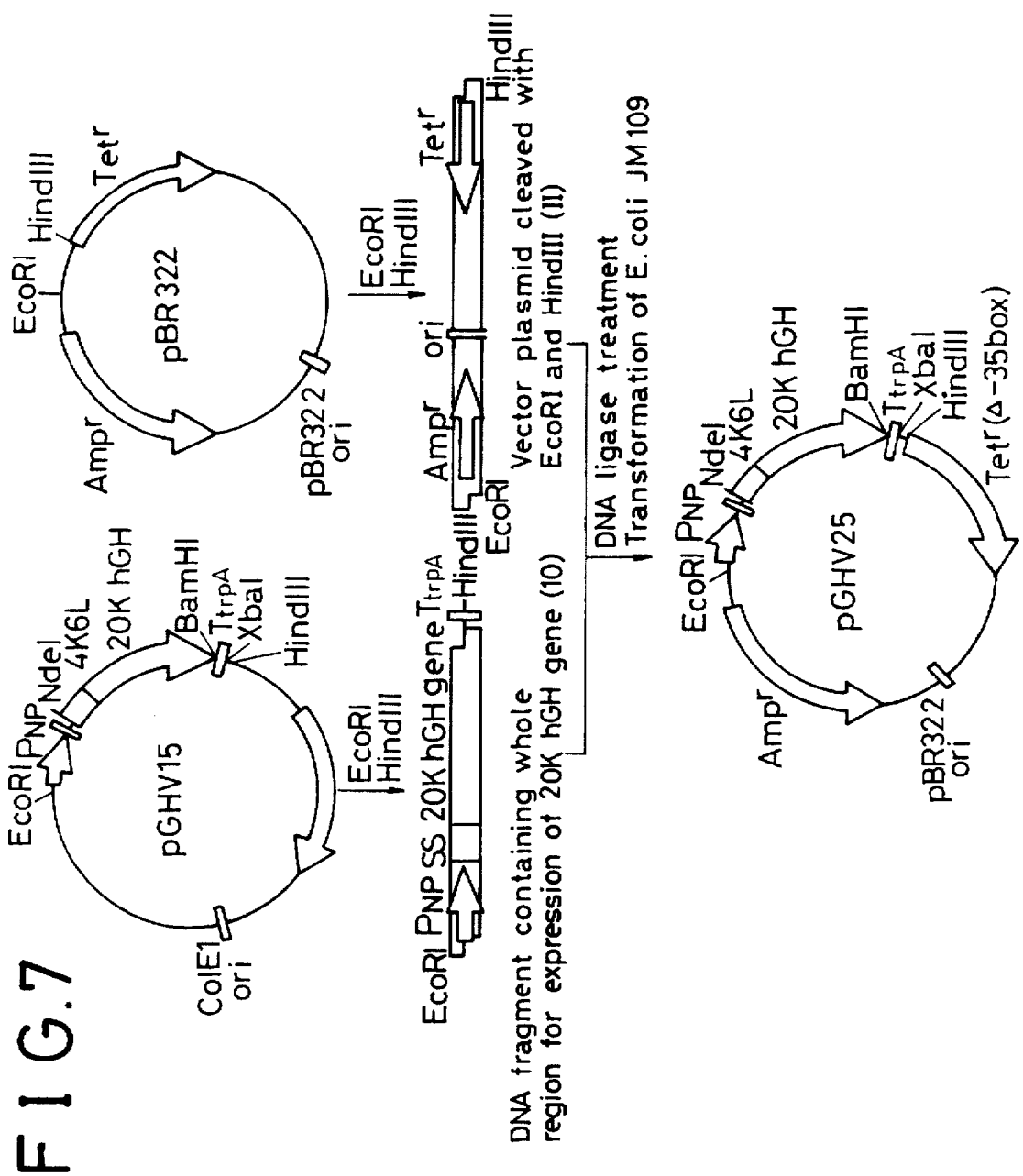
FIG. 7 is a schematic view partially illustrating a preparation method of a 20K hGH secreting plasmid having a drug-resistant marker.
Figure 8:
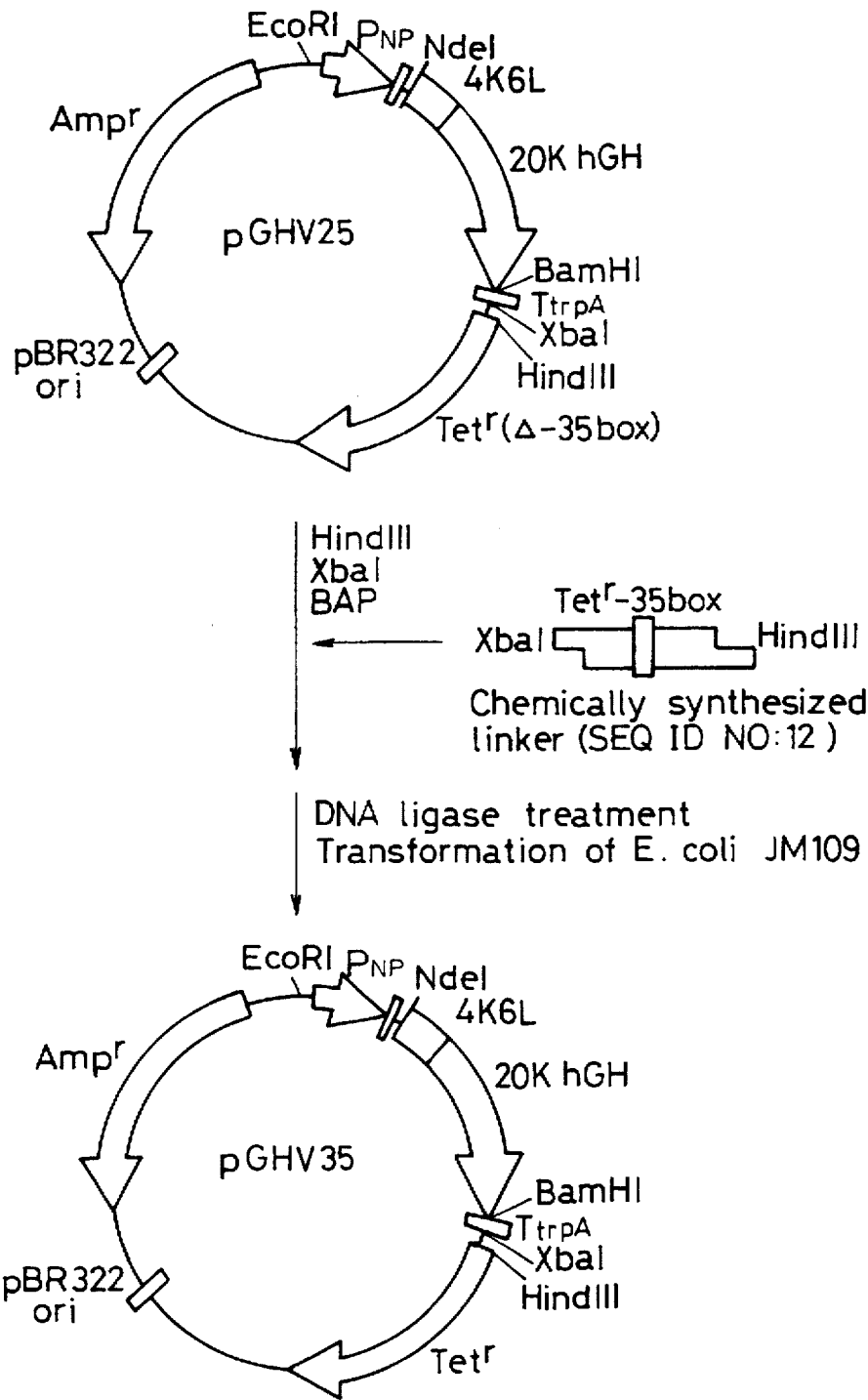
FIG. 8 is a schematic view partially illustrating a preparation method of a 20K hGH secreting plasmid having a drug-resistant marker.

Specifically, a synthetic linker containing a trpA terminator shown by SEQ ID NO: 11 was inserted into a site sandwiched between restriction enzymes BamHI and XbaI of pGHV5 to obtain pGHV15 (FIG. 6). Next, pGHV15 was cut out with the restriction enzymes EcoRI and HindIII to obtain about 0.85 kbp of a DNA fragment (10). On the other hand, pBR322 was cut out with the restriction enzymes EcoRI and HindIII to collect a vector portion (11). The DNA fragment (10) was ligated with the vector portion (11) to prepare pGHV25 (FIG. 7). However, this plasmid was devoid of –35 sequence on the upstream of the HindIII of the tetracycline-resistant gene, and so it showed ampicillin resistance alone but it did not show tetracycline resistance performance. For the purpose of inserting the –35 sequence on the upstream side of the tetracycline gene, a DNA linker shown by SEQ ID NO: 12 was chemically synthesized, and then inserted into a site sandwiched between restriction enzymes XbaI and HindIII of pGHV25 to prepare pGHV35 (FIG. 8). Furthermore, in order to eliminate the ampicillin-resistant gene which pGHV35 had, the region of about 0.8 kbp sandwiched between restriction enzymes EcoRI and VspI so as to fasten ampicillin-resistant gene from a pro-

TABLE 5

The influence of the modification of the secretion signal peptide sequence on the amount of secreted 20K hGH (in terms of mg per liter of a culture medium)

| | Plasmid | | | | | | |
|---|---|---|---|---|---|---|---|
| | pGHW30 | pGHV2 | pGHV3 | pGHV4 | pGHV5 | pGHV6 | pGHV7 |
| Signal peptide | 2K1L | 2K1L | 4K1L | 4K3L | 4K6L | 4K7L | 4K9L |
| Amount of secreted 20K hGH | 28 | 26 | 25 | 24 | 35 | 33 | 30 |

EXAMPLE 4

Figure 9:
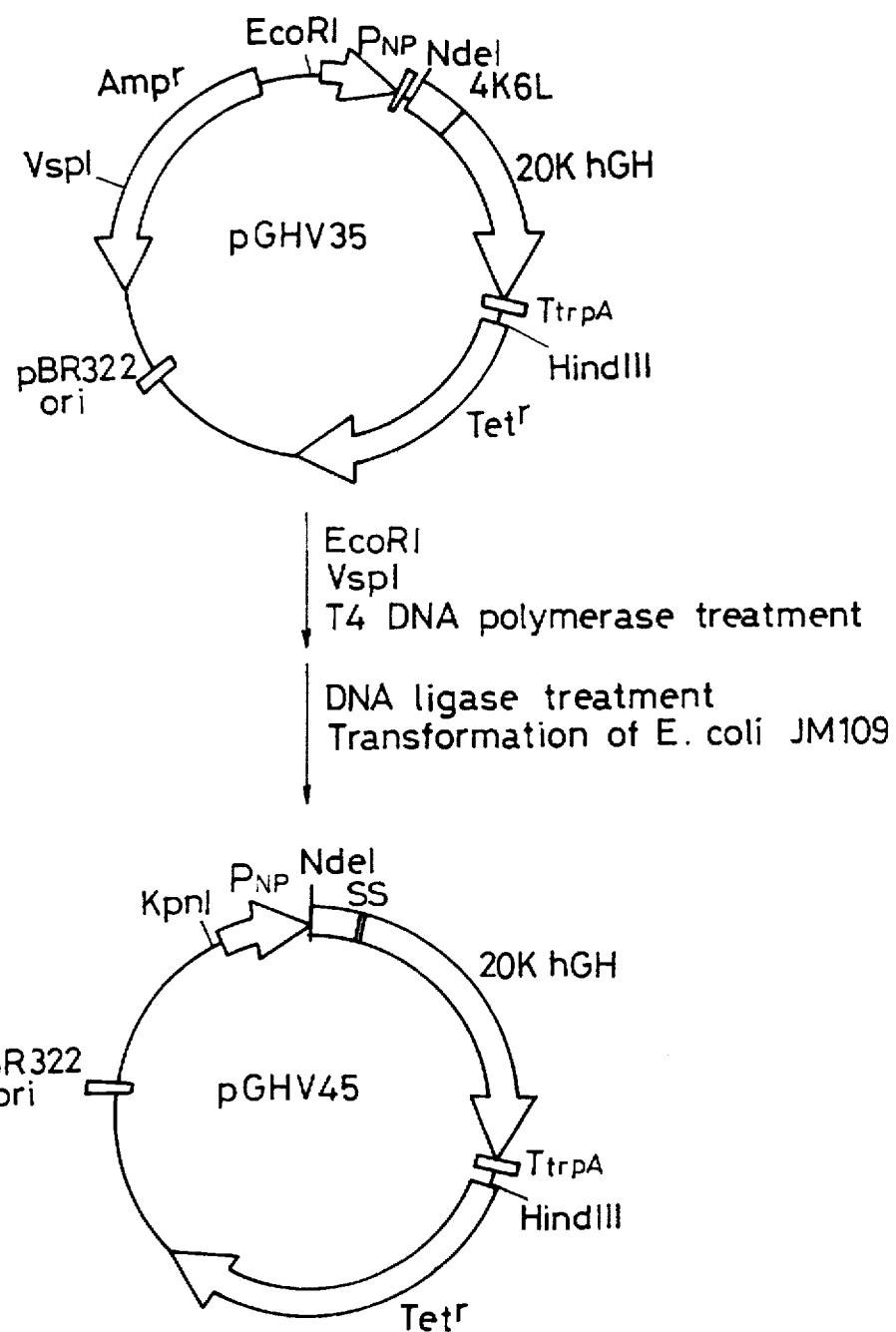
FIG. 9 is a schematic view partially illustrating a preparation method of a 20K hGH secreting plasmid having a drug-resistant marker.

Effect of Coexpression of GR Gene and Modification of Secretion Signal Peptide Sequence on Secretion of 20K hGH (1) Change of Drug-resistant Marker of 20K hGH Secreting Plasmid by Modification of Secretion Signal Peptide Sequence As in Example 1, a GR expressing plasmid and a plasmid for secreting of 20K hGH using a modified secretion signal moter region was deleted to produce pGHV45 (FIG. 9). For a 20K hGH secreting plasmid having another modified signal peptide, a similar operation was carried out to produce pGHV42, pGHV43, pGFV44, pGHV46 and pGHV47.

(2) Secretion of 20K hGH by 20K hGH Secreting Plasmid having Modified Secretion Signal Peptide Coding Region and GR Expressing Plasmid An *Escherichia coli* JM109 strain simultaneously transformed with the 20K hGH secreting plasmid having the modified secretion signal peptide coding region with the obtained tetracycline-resistant marker and the GR expressing plasmid pKKGR1 was added to a culture medium containing IPTG (1 mM), and then cultured in the same manner as in Example 1, and a periplasm fraction was then extracted. Afterward, the content of 20K hGH was measured, and the production of 20K hGH per liter of the culture medium was then calculated. The results are shown in Table 6. In this table, a symbol K represents the Lys residue, and a symbol L represents the Leu residue. The numbers in front of these symbols represent the numbers of the lysine residue and the leucine residue present in the positive charge region and the hydrophobic region after the insertion, respectively.

TABLE 6

The modification effect of the secretion signal peptide sequence under the coexpression of the GR gene (influence on the amount of secreted 20K hGH) (in terms of mg per liter of the culture medium)

| | Plasmid | | | | | | |
|---|---|---|---|---|---|---|---|
| | pGHW30 | pGHV42 | pGHV43 | pGHV44 | pGHV45 | pGHV46 | pGHV47 |
| Signal peptide | 2K1L | 2K1L | 4K1L | 4K3L | 4K6L | 4K7L | 4K9L |
| Amount of secreted 20K hGH | 65 | 63 | 58 | 61 | 76 | 71 | 69 |

Among the 20K hGH plasmids having the modified secretion signal peptides, pGHV45 gave the largest secretion.

EXAMPLE 5

Figure 10:
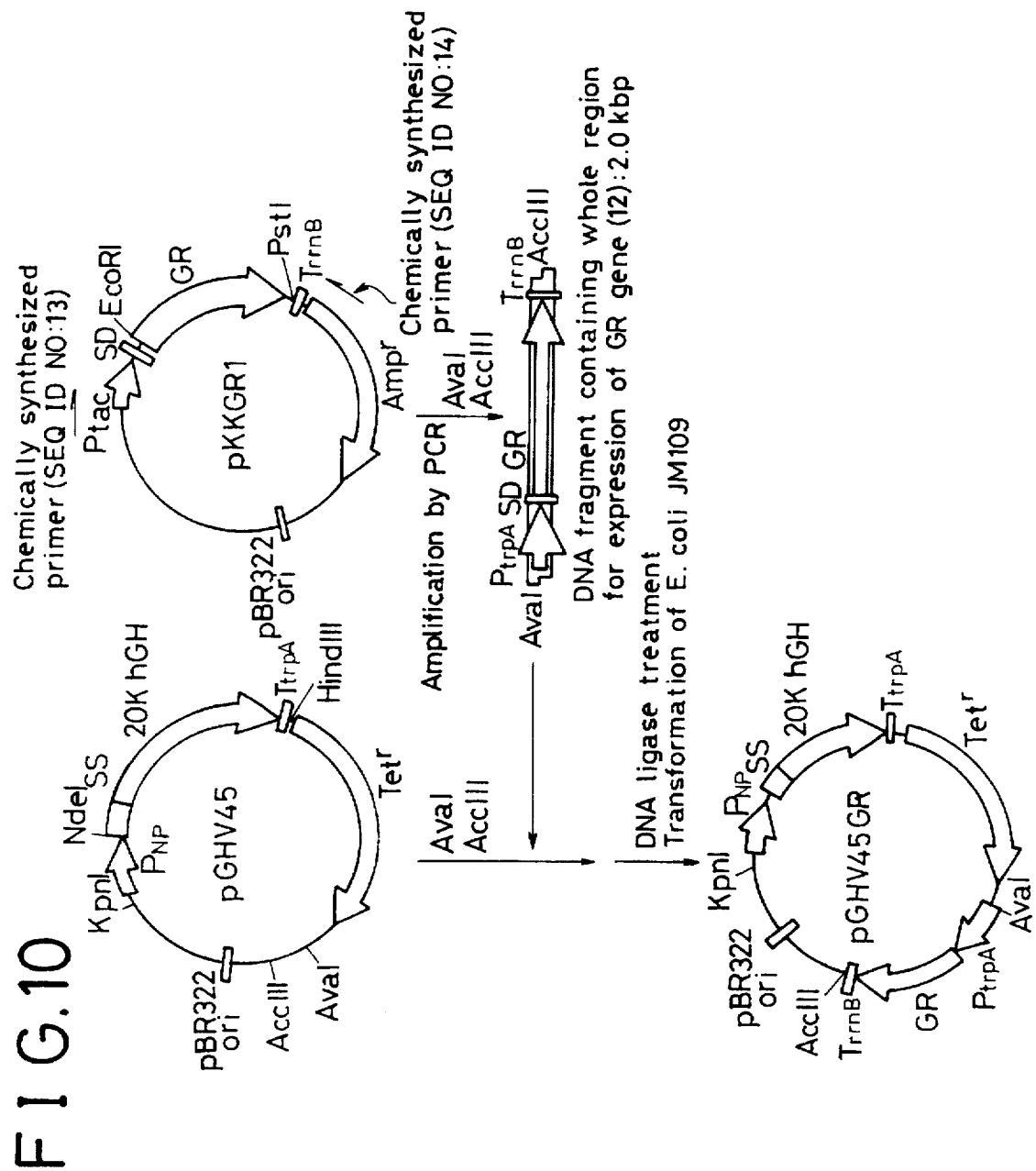
FIG. 10 is a schematic view illustrating a preparation method of a secretory plasmid pGHV45GR containing a GR gene and a 20K hGH gene having a modified secretion signal peptide in the same plasmid.

Production of 20K hGH by Secretory Plasmid Containing 20K hGH Gene with Modified Secretion Signal Peptide Coding Region and GR Gene in the Same Plasmid (1) Production of Secretory Plasmid pGHV45GR Containing 20K hGH Gene with Modified Secretion Signal Peptide Coding Region and GR Gene in the Same Plasmid A region of pKKGR1 containing a tac promoter, a GR gene and a TrrnB terminator was subjected to PCR amplification by the use of a synthetic oligonucleotides shown in SEQ ID NOs: 13 and 14 as primers to obtain about 2.0 kbp of a DNA fragment (12). In this case, the design of each primer was made so that the recognition sequences of restriction enzymes AvaI and AccIII might be present at both the ends of the DNA fragment. Next, the DNA fragment (12) containing a GR gene expressing region was inserted into a site of pGHV45 which was digested with the restriction enzymes AvaI and AccIII to produce pGHV45GR (FIG. 10).

(2) Production of 20K hGH by Use of Secretory Plasmid pGHV45GR Containing 20K hGH Gene with Modified Secretion Signal Peptide Coding Region and GR Gene in the Same Plasmid Various Escherichia coli strains transformed with pGHV45GR were cultured in the same manner as in Example 1, and each periplasm fraction was then extracted. Next, the content of 20K hGH was measured, and the production (mg) of 20K hGH per liter of the culture medium was then calculated. The results are shown in Table 7.

TABLE 7

The productivity of 20K hGH by use of pGHV45GR (in terms of mg per liter of the culture medium)

| | Host | | | | | | | |
|---|---|---|---|---|---|---|---|---|
| | JM109 | | W3110 | | RB791 | | HB101 | |
| Addition of IPTG | − | + | − | + | − | + | − | + |
| Amount of secreted 20K hGH | 73 | 23 | 12 | 7 | 75 | 21 | 9 | 6 |

In the case that JM109 was used as a host and IPTG was added to the culture medium, the amount of the secreted 20K hGH was contrarily small, in contrast to the experimental results of Examples 1, 2 and 3 in which the two different plasmids were used. When the whole cell extract solution prepared by sonication was applied to SDS-PAGE analysis, the excessively high production of GR could be confirmed. On the contrary, under non-inductive culture conditions in which IPTG was not added to the culture medium, a large amount of the secretion was obtained. These cultured cells were similarly analyzed by SDS-PAGE, and as a result, it was confirmed that the amount of the produced GR was smaller than that of the produced GR under the induced culture conditions. From these results, it was apparent that in the transformed JM109 in which 20K hGH gene and the GR gene were present in the same plasmid, the conditions where IPTG was not added to the culture medium were preferable. The GR gene was expressed by the tac promoter, but in the case that the host was the JM109, it could be considered that the induction with the IPTG addition caused the excessively high expression of the GR gene, which leaded to the decrease of the secretion.

In the transformed W3110, a small amount of the secretion was obtained in both the cases of IPTG induction and no IPTG induction, as shown in Table 7. When the whole cell extract solution prepared by sonication was appliced to SDS-PAGE analysis, the excessively high production of the GR could be confirmed. Also in the case that HB101 was used as a host, similar results were obtained.

It could be presumed that the above-mentioned difference due to the different hosts of the JM109 and the W3110 was concerned with presence/absence of lacI$^q$ on the chromosome of each host. That is to say, the JM109 has a lacI$^q$ gene which functions as a repressor of the tac promoter, but the W3110 does not have any lacI$^q$ gene. It was confirmed by the following experiment using RB791 as a host that this hypothesis was correct. The RB791 (ATCC 53622) is a strain prepared by integrating the laciq gene into the W3110, and the other characteristics of the RB791 are the same as in the W3110. In the case that this RB791 was used, the amount of the secreted 20K hGH decreased under the culture conditions of the IPTG induction, as in the case of the JM109, and the high production of the GR was confirmed by the electrophoresis. On the other hand, under the conditions of no IPTG induction, a large amount of the secreted 20K hGH could be obtained, and it was confirmed by the electrophoresis that the excessive production of the GR was not present.

EXAMPLE 6

Utilization in Host Strain having no lacI$^q$ Gene

For the purpose of enabling the utilization of W3110 and HB101 which were undesirable as an *Escherichia coli* host in Example 5, investigations were conducted as described below.

Figure 11:
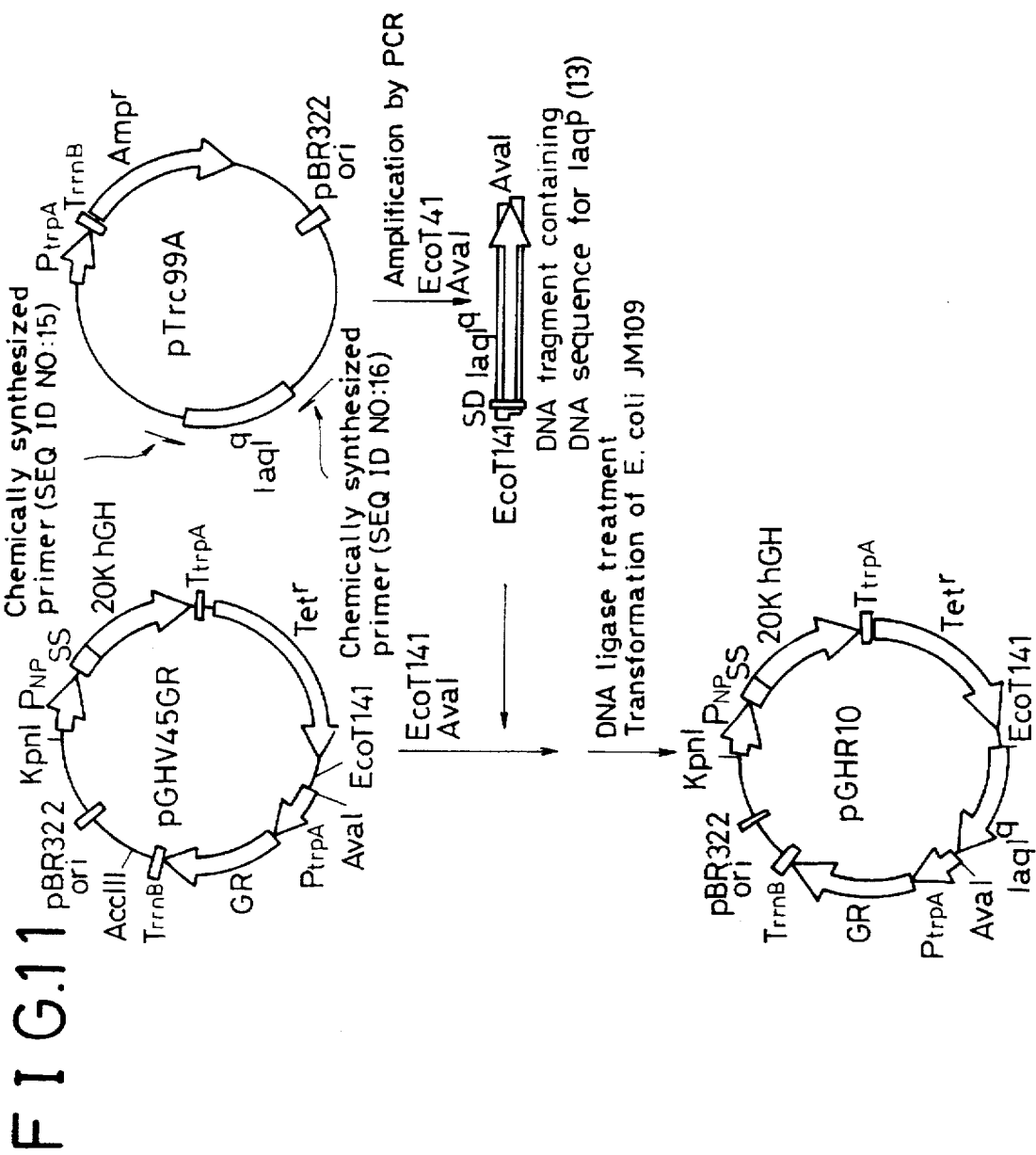
FIG. 11 is a schematic view illustrating a preparation method of a secretory plasmid pGR10 which contains a GR gene and a 20K hGH gene having a modified secretion signal peptide in the same plasmid and which can be utilized even in a host strain having no lacI$^q$ gene.

(1) Production of Secretory Plasmid pGHR10 which Contains 20K hGH Gene with Modified Secretion Signal Peptide Coding Region and GR Gene in the Same Plasmid and which is Effective even in Host (W3110 or HB109) having no lacI$^q$ Gene In order to integrate a lacI$^q$ gene into the same replicon as a 20K hGH gene expressing region, the lacI$^q$ gene of a commercially available expression vector pTrc99A (Pharmacia Labs., Inc.) was subjected to PCR amplification by the use of chemically synthesized oligonucleotides shown in SEQ ID NOs: 15 and 16 as primers to obtain a DNA fragment (13). In this case, the design of each primer was made so that the recognition sites of restriction enzymes EcoT141 and AvaI might be added to both the ends of the DNA fragment (13). Next, pGHV56GR was digested with the restriction enzymes EcoT141 and AvaI to collect a vector fragment (14). This vector fragment (14) was ligated with the DNA fragment (13) containing the lacI$^q$ gene to produce pGHR10 (FIG. 11). The inserted lacI$^q$ gene contains a RBS sequence (a ribosome binding region) alone and does not have any promoter region, and therefore it can be transcribed and expressed by the lead-through of an upstream tetracycline-resistant gene.

(2) Production of 20K hGH by Use of Secretory Plasmid pGHR10 which Contains 20K hGH Gene with Modified Secretion Signal Peptide Coding Region and GR Gene in the Same Plasmid and in which Expression of GR is Controlled by lacI$^q$ gene Various transformed *Escherichia coli* strains transformed with pGHR10 were cultured in the same manner as in Example 1, and each periplasm fraction was then extracted. Next, the content of 20K hGH was measured, and the production (mg) of 20K hGH per liter of the culture medium was then calculated. The results are shown in Table 8. Among the transformed *Escherichia coli* strains, the *Escherichia coli* W3110 strain (MT-10765) carrying pGHR10 is deposited under deposition No. FERM BP-5020. A HB101 strain was gotten from Takara Shuzo Co., Ltd. A LE392 strain (ATCC 33572) was gotten from American Type Culture Collection.

TABLE 8

The production of 20K hGH by use of pGHR10 (in terms of mg per liter of the culture medium)

| Host | W3110 | | HB101 | | LE392 | |
|---|---|---|---|---|---|---|
| Addition of IPTG | − | + | − | + | − | + |
| Amount of secreted 20K hGH | 76 | 10 | 74 | 4 | 68 | 5 |

By the utilization of pGHR10 in which the 20K hGH gene expressing region and the GR gene are present on the same replicon and the lacI$^q$ gene for controlling the expression of the GR gene directed by the promoter (tac) is allowed to exist on the same plasmid, the use of a host strain not having the lacI$^q$ gene on a chromosome becomes also possible.

What is claimed is:

1. A method for secreting a desired recombinantly produced protein into the periplasm of an *Escherichia coli* host cell comprising: expressing a DNA encoding for said desired recombinantly produced protein in an *E. coli* host cell which produces enhanced amounts of glutathione reductase relative to a wild-type *E. coli* host cell.

2. The method of claim 1, wherein said glutathione reductase is encoded by a DNA derived from *E. coli*.

3. The method of claim 1, wherein a DNA encoding glutathione reductase and said DNA encoding the desired recombinantly produced protein are located in a single replicon.

4. The method of claim 2, wherein a DNA encoding glutathione reductase and said DNA encoding the desired recombinantly produced protein are located in a single replicon.

5. A method according to claim 1, wherein a DNA encoding glutathione reductase and said a DNA encoding the desired recombinantly produced protein are located in different replicons.

6. A method according to claim 2, wherein said DNA encoding glutathione reductase and said DNA encoding the desired recombinantly produced protein are located in different replicons.

7. A method for secreting a human growth hormone protein having an approximate molecular weight of 20,000 in an *E. coli* host cell comprising: expressing a DNA encoding for said human growth hormone having an approximate molecular weight of 20,000 in an *E. coli* host cell which has been genetically engineered to produce enhanced amounts of glutathione reductase relative to a non-genetically engineered *E. coli* host cell.

8. The method according to claim 7, wherein said glutathione reductase is encoded by a DNA derived from *E. coli*.

9. A method according to claim 7, wherein a DNA encoding glutathione reductase and said DNA encoding said human growth hormone having an approximate weight of 20,000 are located in a single replicon.

10. A method according to claim 8, wherein said DNA encoding glutathione reductase and said DNA encoding said human growth hormone having an approximate weight of 20,000 kD are located in a single replicon.

11. A method according to claim 7, wherein said DNA encoding said glutathione reductase and said DNA encoding said human growth hormone having an approximate molecular weight of 20,000 are located in different replicons.

12. The method according to claim 8, wherein said DNA encoding said glutathione reductase and said DNA encoding said human growth hormone having an approximate molecular weight of 20,000 are located in different replicons.

13. The method according to claim 7, wherein said DNA encoding said human growth hormone having an approximate molecular weight of 20,000 is operatively linked to a signal peptide having the amino acid sequence contained in SEQ. ID. NO. 1.

14. The method according to claim 8, wherein said DNA encoding said human growth hormone having an approximate molecular weight of 20,000 is operatively linked to a signal peptide having the amino acid sequence contained in SEQ. ID. NO. 1.

* * * * *

UNITED STATES PATENT AND TRADEMARK OFFICE
CERTIFICATE OF CORRECTION

PATENT NO. : 5,759,810

DATED: : June 2, 1998

INVENTOR(S) : Masaru HONJO et al

It is certified that error appears in the above-identified patent and that said Letters Patent is hereby corrected as shown below:

In claim 10, column 28, line 2, delete "kD".

Signed and Sealed this

Sixth Day of April, 1999

Attest:

Q. TODD DICKINSON

*Attesting Officer*  *Acting Commissioner of Patents and Trademarks*